United States Patent
Rivier (12)

(10) Patent No.: US 6,323,312 B1
(45) Date of Patent: *Nov. 27, 2001

(54) CYCLIC CRF ANTAGONIST PEPTIDES

(75) Inventor: Jean E. F. Rivier, La Jolla, CA (US)

(73) Assignee: The Salk Institute For Biological Studies, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/424,127

(22) PCT Filed: May 26, 1998

(86) PCT No.: PCT/US98/10591

§ 371 Date: Nov. 17, 1999

§ 102(e) Date: Nov. 17, 1999

(87) PCT Pub. No.: WO98/54221

PCT Pub. Date: Dec. 3, 1998

Related U.S. Application Data

(63) Continuation-in-part of application No. 08/865,773, filed on May 30, 1997, now Pat. No. 5,777,073, which is a continuation-in-part of application No. 08/556,578, filed on Nov. 10, 1995, now Pat. No. 5,874,227, and a continuation-in-part of application No. 08/353,928, filed on Dec. 12, 1994, now Pat. No. 5,663,292.

(51) Int. Cl.$^7$ .............................. A61K 38/12; C07K 7/64
(52) U.S. Cl. ..................... 530/306; 530/324; 530/317; 514/12; 514/9
(58) Field of Search .................... 530/306, 324, 530/317; 514/12, 9

(56) References Cited

U.S. PATENT DOCUMENTS 5,493,006   2/1996   de Miranda et al. .............. 530/306
5,777,073 * 7/1998   Rivier ............................ 530/306

FOREIGN PATENT DOCUMENTS

WO9003392   4/1990   (WO) .
WO9619499   6/1996   (WO) .

OTHER PUBLICATIONS

Gulyas, et al., *Potent, structurally constrained agonists and competitive antagonists of corticotropin–releasing factor*, Proc. Natl. Acad. Sci. U.S.A,, vol. 92, 10575–10579 Nov. 1995, Pharmacology.

* cited by examiner

*Primary Examiner*—Christopher S. F. Low
*Assistant Examiner*—Anish Gupta
(74) *Attorney, Agent, or Firm*—Fitch, Even, Tabin & Flannery

(57) ABSTRACT

Novel cyclic CRF antagonist peptides are created by shortening the N-terminus of a CRF family peptide by 8 residues and adding an acyl group. CML is present in what would be the 27-position of the native CRF sequence, and a cyclizing bond is created between the side chains of the residues in positions 30 and 33. The side chain of Lys, preferably, in position 33 is linked to the side chain of Glu in position 30 by a lactam bridce. Disclosed CRF antagonists include: (cyclo 30–33)[Ac-Asp$^9$, D-Phe$^{12}$, Nle$_{21,38}$, CML$^{27,40}$, Glu$^{30}$, Lys$^{33}$]r/hCRF(9-4); (cyclo 30–33)[Ac-Asp$^9$, D-Phe$^{12}$, CML$^{18,27}$, Nle$^{21,38}$, Glu$^{30}$, Lys$^{33}$]r-hCRF(9–41); (cyclo 30–33)[Ac-Asp$^9$, D-Phe$^{12}$, Nle$^{21,38}$, CML$^{27,37}$, Glu$^{30}$, Lys$^{33}$]r/hCRF(9–41); (cyclo 30–33)[Ac-Asp$^9$, D-Phe$^{12}$, CML$^{14,27}$, Nle$^{21,38}$, Glu$^{30}$, Lys$^{33}$]r/hCRF(9–41); (cyclo 30–33)[Ac-Asp$^9$, D-Phe$^{12}$, Nle$^{21,38}$, CML$^{27}$, Glu$^{30}$, Lys$^{33}$]r/hCRF(9–41); and (cyclo 30–33)[Ac-Asp$^9$, D-Phe$^{12}$, Nle$^{21,38}$, CML$^{27,40}$, Glu$^{30}$, Aib$^{32}$, Lys$^{33}$]r/hCRF(9–41).

18 Claims, No Drawings

CYCLIC CRF ANTAGONIST PEPTIDES

This application is a 371 of PCT/US98/10591 filed May 26, 1998 which is a continuation-in-part of Ser. No. 08/865,773, filed May 30, 1997 and now U.S. Pat. No. 5,777,073 which is a CIP of Ser. No. 08/556,518 filed Nov. 11, 1995, now U.S. Pat. No. 5,874,227, which is a CIP of Ser. No. 08/353,928 filed Dec. 12, 1994 now U.S. Pat. No. 5,663,292.

This invention is generally directed to peptides and to the pharmaceutical treatment of mammals using such peptides. More specifically, the invention relates to cyclic antagonists of the CRF hentetracontapeptides as well as to members of the larger family of CRF-like peptides, to pharmaceutical compositions containing such cyclic CRF antagonists, to methods of treatment of mammals using such cyclic CRF antagonists, and to methods of screening for new drugs using such peptides.

Ovine CRF (oCRF) (SEQ ID NO:1), in 1981, was the first physiologic corticotropin releasing factor characterized; it is disclosed in U.S. Pat. No. 4,415,558 as a 41-residue amidated peptide which lowers blood pressure in mammals when injected peripherally and stimulates the secretion of ACTH and β-endorphin.

Rat CRF (rCRF) (SEQ ID NO:2) was later isolated, purified and characterized; it is described in U.S. Pat. No. 4,489,163. The amino acid sequence of human CRF was determined to be the same as that of rCRF, so rCRF and hCRF are used interchangeably, as is the designation r/hCRF. These peptide hormones are considered to form a part of a larger family of native CRF-like peptides and analogs which include the mammalian and fish CRFs, the urotensins and sauvagine (SEQ ID NO:3).

A CRF analog having a high alpha-helical forming potential was developed in about early 1984. It is a 41-residue amidated peptide commonly referred to as AHC (alpha-helical CRF) (SEQ ID NO:4) which is described in U.S. Pat. No. 4,594,329 and is considered to be a member of the overall family of CRF-like peptides. Other CRF analogs containing D-isomers of α-amino acids were developed, such as those shown in U.S. Pat. No. 5,278,146. Synthetic r/hCRF, oCRF and AHC all stimulate ACTH and β-endorphin-like activities (β-END-Li) in vitro and in vivo and substantially lower blood pressure when injected peripherally. Antagonists of these three peptides and of sauvagine and urotensin are disclosed in U.S. Pat. No. 4,605,642, issued Aug. 12, 1986. Cyclic CRF antagonists exhibiting biopotency are disclosed in U.S. Pat. Nos. 5,493,006 and in 5,510,458 and published international application WO 96/19499, the latter two of which disclose cyclizing bonds between the residues in the 30 and 33 positions. More specifically, the latter document discloses a potent CRF antagonist referred to as Destressin having the formula (cyclo-33) [D-Phe$^{12}$, Nle$^{21,38}$, Glu$^{30}$, D-His$^{32}$, Lys$^{33}$]-r/hCRF(12–41).

Since the foregoing discoveries, the search for still further improved CRF antagonists has continued.

CRF antagonist peptides have now been discovered which exhibit further increased biological activity in comparison to known CRF antagonists, and many exhibit substantially no residual CRF agonist activity. They also exhibit high solubility in neutral aqueous solutions, e.g. at physiological pH, and high receptor affinity.

It is also shown that the various members of the family of CRF-like peptides can be modified to create such highly biopotent CRF antagonists that bind strongly to the known CRF receptors (CRF-R) without significantly activating same and thus block the action of CRF at its receptors. They exhibit an affinity for CRF-R well above that exhibited by oCRF.

In one basic aspect, the invention provides a cyclic CRF antagonist peptide which binds to CRF receptors but has an intrinsic activity with respect to such receptors equal to 20% or less than that of native CRF, which peptide has the formula Y-A-D-Xaa-B-Xaa$_c$-Xaa$_a$,-Xaa$_b$-Xaa$_c$-C-NH$_2$ wherein: Y is an acyl group having up to 15 carbon atoms; A is Asp-Leu-Thr or Asp-Leu-Ser; D-Xaa is D-Phe, D-2Nal or D-Leu; B is a sequence of 17 amino acid residues of a peptide of the CRF family selected from the group of sequences consisting of (a) residues 13–29 of mammalian and fish CRFs and of fish urotensins and (b) residues 12–28 of sauvagine; Xaa$_c$n, represent a pair of amino acid residues, the side chains of which are linked in a cyclizing bond; Xaa$_a$ is a natural α-amino acid residue other than Cys; Xaa$_b$ is a residue of either (c) a D-isomer amino acid from the group consisting of D-isomers of natural α-amino acids other than Cys and unnatural aromatic α-amino acids, or (d) a natural L-isomer α-amino acid other than Cys; and C is a sequence of the last 8 amino acid residues of the C-terminal portion of a peptide of the CRF family selected from the group of sequences consisting of (e) residues 34–41 of mammalian and fish CRFs and of fish urotensins and (f) residues 33–40 of sauvagine; provided that CML is present as residue-27 in sequence (a), or as residue-26 in sequence (b) and wherein Nle may be substituted for Met in said peptide sequences.

It has been found that the combination of such a cyclizing bond, the presence of CML$^{27}$ and the acylation of the N-terminus in a peptide of 33 residues in length creates a molecule of long-acting duration and high biopotency, e.g. (cyclo 30–33)[Ac-Ser$^9$, CML$^{27}$, Glu$^{30}$, Lys$^{33}$]-r/hCRF (9–41). The family of CRF-like peptides is considered to encompass those peptides which bind to the CRF receptors and have at least about 45% amino acid structural homology with ovine CRF, the first mammalian CRF isolated and characterized. The CRF-like family includes the following known peptides: ovine CRF (SEQ ID NO:1), rat/human CRF (SEQ ID NO:2), porcine CRF (SEQ ID NO:5), bovine CRF (SEQ ID NO:6), fish CRFs (SEQ ID NO:7), α-helical CRF(AHC) (SEQ ID NO:4), carp urotensin (SEQ ID NO:8), sucker urotensin (SEQ ID NO:9), maggy sole urotensin (SEQ ID NO:10), flounder urotensin (SEQ ID NO:11) and sauvagine (SEQ ID NO:3).

As indicated above, these peptides have a cyclizing bond between the residues in what would be the 30- and 33-positions in mammalian CRF. A second such bond may optionally be provided between the residues in the 20- and 23-positions. Preferably, the cyclizing bond is a lactam bridge (amide bond) between a side chain carboxyl group on the residue in the 30-position, preferably Glu, and a side chain amino group on the 33-position residue, preferably Lys or Orn. Although the naturally occurring residues of the CRF-like family may be present in the position which corresponds to the 32-position of CRF, i.e. His, Gly, Leu, Gln and Ala, it appears that any α-amino acid is tolerated here. Preferably however, a basic and/or aromatic D-isomer residue or an equivalent is present in the 32-position in the region between the residues joined by this lactamn bridge, e.g. D-His, D-Arg, D-Tyr, imBzlD-His, D-Nal D-Pal, D-Trp, D-Dpr(Nic), DAph, D-Agl(Nic), D-Orn, D-Dbu, D-Dpr, D-Orn(Nic) or a comparable D-isomer. However, a wide variety of other residues such as D-Ala, D-Glu, D-Asn, Aib, Asn, Pal, Nal, Phe and Tyr may be present.

As described herein, the lactam linkage between the side chains of the residues in the 30- and 33-positions is preferred; however, biopotency is also increased, but to a somewhat lessor degree, by alternative cyclizing linkages in this same region of the molecule. For example, the side chain of Glu[28] or Glu[29] can be linked respectively to Lys[31] or Lys[32], or instead respectively to Lys[32] or Lys[33] (creating a one-residue longer span). These somewhat less biopotent alternatives are considered to be equivalents to the 30–33 cyclizing linkage.

These peptides also have the preferred inclusion of D-Phe, D-2Nal or D-Leu or an equivalent D-isomer, e.g., D-Cpa, D-Tyr, D-Trp or D-3Pal, in the 12-position, and they preferably have norleucine substituted for any naturally occurring Met, e.g., in the 21 and 38 positions of r/h CRF. If it is desired to provide a labelled peptide for use in a binding or other assay, as more fully discussed in WO 96/19499, as by adding a radioactive isotope or a fluorescent dye as is well known in this art, D-Tyr, Tyr (e.g. Ac-D-Tyr or Ac-Tyr) or an acyl group having a hydroxy aryl moiety (e.g. desNH$_2$-Tyr) may be present at the N-terminus to form equivalents which are suitable for labelling. other optional substitutions may also be made throughout the molecule as generally known, and these are considered to be functional equivalents of the specific peptides described hereinafter.

In a broader aspect, the invention provides a cyclic peptide which is an antagonist of CRF, said peptide having the formula:

(cyclo 30–33)Y-Asp-R$_{10}$-R$_{11}$-D-Phe-R$_{13}$-R$_{14}$-R$_{15}$-Arg-R$_{17}$-R$_{18}$-R$_{19}$-R$_{20}$-R$_{21}$-R$_{22}$-R$_{23}$-R$_{24}$-R$_{25}$-R$_{26}$-CML-R$_{28}$-R$_{29}$-Glu-R$_{31}$-R$_{32}$-R$_{33}$-R$_{34}$-Arg-R$_{36}$-R$_{37}$-R$_{38}$-R$_{39}$-R$_{40}$-R$_{41}$-NH$_2$ wherein Y is an acyl group having up to 15 carbon atoms; R$_{10}$ is Leu or CML; R$_{11}$ is Thr or Ser; R$_{13}$ is His, Tyr or Glu; R$_{14}$ is CML or Leu; R$_{15}$ is Leu or CML; R$_{17}$ is Glu, CML, Asn or Lys; R$_{18}$ is Val, Nle, CML or Met; R$_{19}$ is Leu or Ile; R$_{20}$ is Glu, D-Glu, or His; R$_{21}$ is Nle or Met; R$_{22}$ is Ala, D-Ala, Aib, Asp, Thr, D-Thr, Glu or D-Glu; R$_{23}$ is Arg or Lys; R$_{24}$ is Ala, Aib or CML; R$_{25}$ is Glu or Asp; R$_{26}$ is Gln, Asn or Lys; R$_{28}$ is Ala, Lys, Aib or Arg; R$_{29}$ is Gln, Aib or Glu; R$_{31}$ is Aib or an L-isomer of an α-amino acid other than Cys; R$_{32}$ is Aib or a D- or L-isomer of an α-amino acid other than Cys; R$_{33}$ is Lys or Orn; R$_{34}$ is Asn or Aib; R$_{36}$ is Lys, Orn, Arg, Har, CML or Leu; R$_{37}$ is CML, Leu or Tyr; R$_{38}$ is Nle, Met or CML; R$_{39}$ is Glu, Aib or Asp; R$_{40}$ is CML, Ile, Aib, Thr, Asn, Glu, Ala, Val, Leu, Nle, Phe, Nva, Gly or Gln; and R$_{41}$ is Ala, Aib, Ile, Gly, Val, Leu, CML, Nle, Phe, Nva or Gln; wherein D-Phe[12] may be substituted by another D-amino acid, such as D-Leu, D-Tyr, D-Trp, D-Cpa, D-Trp, D-Nal or D-Pal, or by Phe or Tyr.

Of particular interest are those analogs wherein the Leu residue in the 27-position is substituted with a methyl group on its α-carbon atom, i.e., CML. CML may optionally also be present in the 10-, 14-, 15-, 17-, 18-, 24-, 36-, 37-, 38-, 40- and/or 41-positions, and analogs including CML[27] and at least one more such CML residue are preferred. In addition, CML may be substituted in the 19-position and the 21-position to provide equivalent analogs. C$^α$MeAla(CMA), which is α-aminoisobutyric acid (Aib), may also be optionally inserted at one or more of positions 22, 24, 28, 29, 31, 32, 34, 39, 40 and 41. Such substitutions, both alone and in combination with various of the aforementioned substitutions, are considered to enhance biopotency and/or to increase duration of action. For example, the combination of CML[27] with one or more of CML[18], and CML[40] and/or with one or more of Aib[22], Aib[24], Aib[28], Aib[31] and Aib[32] (together with the 30–33 side chain bridge) provides long duration of bioactivity.

Pharmaceutical compositions in accordance with the invention include such CRF antagonists or nontoxic addition salts thereof that are dispersed in a pharmaceutically acceptable liquid or solid carrier. Some such formulations are facilitated because of high solubility at physiological pH; however, formulations in aqueous solutions of mannitol or corn oil may be preferred for subcutaneous (s.c.) administration. The administration of such peptides or pharmaceutically acceptable addition salts thereof to mammals, particularly humans, in accordance with the invention may be carried out for the regulation of secretion of ACTH, β-endorphin, β-lipotropin, corticosterone and other products of the pro-opiomelano-cortin (POMC) gene and/or for affecting mood, behavioral and gastrointestinal functions and autonomic nervous system activities. For example, these CRF antagonists may be administered to reduce high ACTH levels, and thereby treat stress-related illnesses, such as stress-induced depression and anxiety, to raise blood pressure when injected iv, to decrease blood flow to the gastrointestinal tract, i.e. particularly to treat patients suffering from irritable bowel syndrome and gastrointestinal diseases, and also to treat inflammatory disorders; immune suppression; human immunodeficiency virus (HIV) infections; Alzheimer's disease; anorexia nervosa; hemorrhagic stress; drug and alcohol withdrawal symptoms; drug addiction, and fertility problems. Because of these broad effects, it may be desirable to administer these peptides with hormonal replacement therapy as discussed hereinafter.

The peptides also provide the basis for valuable methods for drug screening in order to detect even more potent molecules that will bind to and/or activate CRF receptors as a result of their high affinity for CRF receptors.

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine, Orn=L-ornithine, Nle=L-norleucine, Nva=L-norvaline, Agl=aminoglycine, Dbu=L-2,4-diaminobutyric acid, Dpr=L-2,3-diaminopropionic acid, Hly=L-homolysine and Har=L-homoarginine. In addition the following abbreviations are used: CML=C$^α$CH$_3$-L-leucine; Aib=C$^α$CH$_3$-alanine or 2-aminoisobutyric acid; Nal=L-β-(1- or 2-naphthyl)alanine; Pal=L-β-(2-, 3- or 4-pyridyl)alanine; Cpa=L-(2-, 3-, or 4-chloro)phenylalanine; Aph=L-(2-,3-or 4-amino) phenylalanine; Amp=(2-, 3- or 4-aminomethyl) phenylalanine; Nic=3-carboxypyridine (or nicotinic acid); Pn=propionyl; iPn=isopropionyl; butyryl=Bt; valeryl=vl; Vac=vinylacetyl; Nph=naphthoyl; and Flu=fluorenoyl. Generally, the CRF antagonists include a D-isomer in the 12-position and may include a D-isomer in the 32-position.

In one particular aspect, the invention provides CRF antagonist peptides (and equivalent nontoxic salts thereof) having the formula:

(cyclo 30–33)Y-Asp-Leu-Thr-R$_{12}$-His-R$_{14}$-Leu-Arg-Glu-R$_{18}$-R$_{19}$-R$_{20}$-R$_{21}$-R$_{22}$-R$_{23}$-R$_{24}$-R$_{25}$-Gln-CML-R$_{28}$-Gln-Glu-R$_{31}$-R$_{32}$-R$_{33}$-R$_{34}$-Arg-R$_{36}$-R$_{37}$-Nle-R$_{39}$-R$_{40}$-R$_{41}$-NH$_2$ wherein Y is an acyl group having not more than 7 carbon atoms; R$_{12}$ is D-Phe or D-2Nal; R$_{14}$ is Leu or CML; R$_{18}$ is Val, CML or Nle; R$_{19}$ is Leu or Ile; R$_{20}$ is Glu or D-Glu; R$_{21}$ is Nle or Met; R$_{22}$ is Ala, D-Ala, Aib or Thr; R$_{23}$ is Arg or Lys; R$_{24}$ is Ala or Aib; R$_{25}$ is Asp or Glu; R$_{28}$ is Ala or Aib; R$_{31}$ is Ala or Aib, R$_{32}$ is D-His, imBzlD-His, D-Arg, D-2Nal, or a D-isomer of another basic and/or aromatic α-amino acid; R$_{33}$ is Lys or Orn; R$_{34}$ is Aib or Asn; R$_{36}$ is Lys or CML; R$_{37}$ is Leu or CML; R$_{39}$ is Glu or Asp; R$_{40}$ is Ile, CML or Aib; and $R_{41}$ is Ala, Aib, CML or Ile. Generally, in all these peptides, D-Phe$^{12}$ may be substituted by another D-amino acid, such as D-Leu, D-Tyr, D-Cpa, D-Nal, D-Trp or D-Pal, or by Phe or Tyr. As an alternative to acylation at the N-terminus, a sulfonamide may be formed, or a sugar or a lipid can be added to modulate hydrophilicity and therefore duration of action and solubility. As earlier indicated, there is wide latitude for selection of the residue in position-32, and examples of suitable additional residues for $R_{32}$ include the D- and L-isomers of Asn, Trp, Arg, Nal, imBzlHis, Tyr, Ala, Leu, Val, Ser, Thr, Cpa, Pal, Lys, Phe and Gln, as well as Aib, Gly, D-Dpr(Nic), D-Aph, D-Agl (Nic), D-Orn, D-Dbu, D-Dpr, or D-Orn(Nic).

In another aspect, the invention provides CRF antagonist peptides (including nontoxic salts thereof) having the following formula:

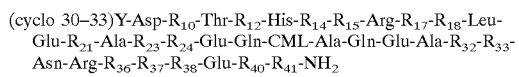

wherein Y is Ac, For or Acr; $R_{10}$ is Leu or CML; $R_{12}$ is D-Phe or D-2Nal; $R_{14}$, $R_{15}$, and $R_{37}$ are independently Leu or CML; $R_{17}$ is Glu or CML; $R_{18}$ is Val or CML; $R_{21}$ is Met or Nle; $R_{23}$ is Arg or Lys; $R_{24}$ is Ala or CML; $R_{32}$ is His, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{36}$ is Lys or CML; $R_{38}$ is Met, Nle or CML; and $R_{40}$ and $R_{41}$ are independently Ile or CML; and wherein at least one of $R_{14}$, $R_{18}$, $R_{36}$, $R_{37}$, $R_{40}$ and $R_{41}$ is CML.

In still another aspect, the invention provides peptides (including nontoxic salts thereof) having the formula:

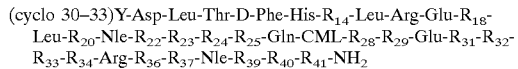

wherein Y is Ac, Acr or For; $R_{14}$ is Leu or CML; $R_{18}$ is Val, CML or Nle; $R_{20}$ is Glu or D-Glu; $R_{22}$ is Ala, Aib, D-Ala or Thr; $R_{23}$ is Arg or Lys; $R_{24}$ is Ala or Aib; $R_{25}$ is Asp or Glu; $R_{28}$ is Ala or Aib; $R_{29}$ is Gln or Glu; $R_{31}$ is Ala or Aib; $R_{32}$ is His, D-His, D-Arg, imBzlD-His, D-Nal, D-Glu, D-Ala, D-Pal, D-Trp, D-Dpr(Nic), D-Aph, D-Agl(Nic), D-Orn, D-Dbu, D-Dpr or D-orn(Nic); $R_{33}$ is Lys or Orn; $R_{34}$ is Asn or Aib; $R_{36}$ is Lys, CML or Leu; $R_{37}$ is Leu or CML; $R_{39}$ is Glu or Asp; $R_{40}$ is Ile, CML, Aib or Glu; and $R_{41}$ is Ile, Aib, CML or Ala; provided that D-2Nal or D-Leu or Phe may be substituted for D-Phe.

When it is desired that any of these peptides should very closely resemble r/hCRF, all or a majority of the following selections are incorporated: $R_{18}$ is Val, $R_{22}$ is Ala, $R_{23}$ is Arg, $R_{24}$ is Ala, $R_{25}$ is Glu, $R_{28}$ is Ala, $R_{39}$ is Glu, and $R_{41}$ is Ile.

In yet another aspect, the invention provides CRF antagonist peptides (including nontoxic salts thereof) having the following formula:

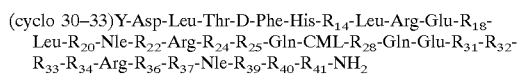

wherein Y is Ac, Acr or For; $R_{14}$ is Leu or CML; $R_{18}$ is Val, CML or Nle; $R_{20}$ is Glu or D-Glu; $R_{22}$ is Ala or Aib; $R_{24}$ is Ala or Aib; $R_{25}$ is Asp or Glu; $R_2$. is Ala or Aib; $R_{31}$ is Ala or Aib; $R_{32}$ is His, Aib, D-His, D-Arg, D-Nal, D-Glu, D-Ala, D-Pal, D-Trp, D-Aph, D-Orn, D-Dbu or D-Dpr; $R_{33}$ is Lys or Orn; $R_{34}$ is Asn or Aib; $R_{36}$ is Lys or CML; $R_{37}$ is Leu or CML; $R_{39}$ is Glu or Asp; $R_{40}$ is Ile, CML or Aib; and $R_{41}$ is Ile, Aib, CML or Ala; provided that D-2Nal or D-Leu or Phe may be substituted for D-Phe.

In a further aspect, the invention provides CRF antagonist peptides (including nontoxic salts thereof) having the formula:

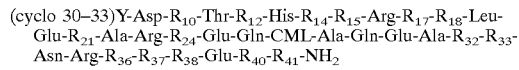

wherein Y is Ac, For or Acr; $R_{10}$ is Leu or CML; $R_{12}$ is D-Phe or D-2Nal; $R_{14}$, $R_{15}$, and $R_{37}$ are independently Leu or CML; $R_{17}$ is Glu or CML; $R_{18}$ is Val or CML; $R_{21}$ is Met or Nle; $R_{24}$ is Ala or CML; $R_{32}$ is His, Aib, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{36}$ is Lys or CML; $R_{38}$ is Met, Nle or CML; and $R_{40}$ and $R_{41}$ are independently Ile or CML; and wherein at least one of $R_{10}$, $R_{14}$, $R_{15}$, $R_{17}$, $R_{18}$, $R_{19}$, $R_{37}$, $R_{40}$ and $R_{41}$ is CML. Specific analogs of this group which are considered to be particularly biopotent from the standpoint of reducing high ACTH levels and raising blood pressure are:

cyclo(30–33)[Ac-Asp$^9$, D-Phe$^{12}$, CML$^{14,27}$, Nle$^{21,38}$, GlU$^{30}$, DHis$^{32}$, Lys$^{33}$]r/hCRF(9–41);

cyclo(30–33)[Ac-Asp$^9$, D-Phe$^{12}$, CML$^{18,27}$, Nle$^{21,38}$, Glu$^{30}$, D-His$^{32}$, Lys$^{33}$]r/hCRF(9–41);

cyclo(30–33)[Ac-Asp$^9$, D-Phe$^{12}$, Nle$^{21,38}$, CML$^{27,36,37}$, Glu$^{30}$, Lys$^{33}$]r/hCRF(9–41);

cyclo(30–33)[Ac-Asp$^9$, D-Phe$^{12}$, Nle$^{21,38}$, CML$^{27,40}$ Glu$^{30}$, Lys$^{33}$]r/hCRF(9–41)

cyclo(30–33)[Ac-Asp$^9$, D-Phe$^{12}$, Nle$^{21,38}$, CML$^{27,37}$, Glu$^{30}$, Lys$^{33}$]r/hCRF(9–41);

cyclo(30–33)[Ac-Asp$^9$, D-Phe$^{12}$, CML$^{14,27,40}$, Nle21,38, Glu$^{30}$, Lys$^{33}$]r/hCRF(9–41);

cyclo(30–33)[Ac-Asp$^9$, D-Phe$^{12}$, Nle$^{21,38}$, CML$^{27,37,41}$, Glu$^{30}$, Lys$^{33}$]r/hCRF(9–41);

cyclo(30–33)[Ac-Asp$^9$, D-Phe$^{12}$, Nle$^{21,38}$, CML$^{14,27,37,40}$, Glu$^{30}$, Lys$^{33}$]r/hCRF(9–41);

cyclo(30–33)[Ac-Asp$^9$, D-2Nal$^{12}$, CML$^{14,27,37,40}$, Nle$^{21,38}$, Glu$^{30}$, Lys$^{33}$]r/hCRF(9–41); and cyclo(30–33)[Ac-Asp$^9$, D-Phe$^{12}$, Nle$^{21,38}$, CML$^{27,37,40}$, Glu$^{30}$, Lys$^{33}$]r/hCRF(9–41).

In a still further aspect, the invention provides CRF antagonist peptides (including nontoxic salts thereof) having the formula:

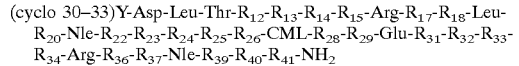

wherein Y is an acyl group having not more than 7 carbon atoms; $R_{12}$ is D-Phe, D-Leu, D-2Nal or D-Tyr; $R_{13}$ is His, Tyr or Glu; $R_{14}$ is Leu or CML; $R_{15}$, is Leu or CML; $R_{17}$ is Glu or CML; $R_{18}$ is Val, CML, Nle or Met; $R_{20}$ is Glu or D-Glu; $R_{22}$ is Ala, D-Ala, Aib, Thr, Asp or Glu; $R_{23}$ is Arg or Lys; $R_{24}$ is Ala, Aib or CML; $R_{25}$ is Asp or Glu; $R_{26}$ is Gln, Asn or Lys; $R_{28}$ is Ala or Aib; $R_{29}$ is Gln, Aib or Glu; $R_{31}$ is Ala or Aib; $R_{32}$ is His, D-His, Aib, D-Arg, D-2Nal, D-3Pal, D-Trp, imBzlD-His, Gly, Tyr, D-Tyr, Leu, D-Leu, Ala or D-Ala; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Asn or Gln; and $R_{41}$ is Ala, Aib, Ile, CML, Val or Phe, provided that at least one of $R_{18}$ and $R_{40}$ is CML.

In a yet further aspect, the invention provides CRF antagonist peptides (including nontoxic salts thereof) having the formula:

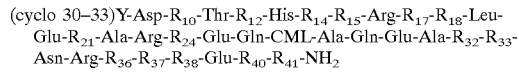

wherein Y is Ac, For or Acr; $R_{10}$ is Leu or CML; $R_{12}$ is D-Phe or D-2Nal; $R_{14}$, $R_{15}$, and $R_{37}$ are independently Leu or CML; $R_{17}$ is Glu or CML; $R_{18}$ is Val or CML; $R_{21}$ is Met or Nle; $R_{24}$ is Ala or CML; $R_{32}$ is His, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{36}$ is Lys or CML; $R_{38}$ is Met, Nle or CML; and $R_{40}$ and $R_{41}$ are independently Ile or CML; and wherein at least one of $R_{18}$, and $R_{40}$ is CML.

In still another aspect, the invention provides CRF antagonist peptides (including nontoxic salts thereof) having the formula: (cyclo 30–33)Y-Asp-Leu-Thr-$R_{12}$-His-Leu-Leu-Arg-Glu-Val-Leu- Glu-Nle-Ala-$R_{23}$-Ala-Glu-Gln-CML-Ala-Gln-Glu-Ala-His-$R_{33}$-Asn- Arg-Lys-Leu-Nle-Glu-Ile-Ile-NH$_2$ wherein Y is Ac or Acr; $R_{12}$ is D-Phe or D-2Nal; $R_{23}$ is Arg or Lys; $R_{33}$ is Lys or Orn; and wherein His$^{32}$ may optionally be substituted by D-His, imBzlD-His, D-Arg, D-Tyr, D-Nal, D-Pal, D-Trp, D-Asn, D- Lys, D-Dpr (Nic), D-Aph, D-Phe, D-Cpa, D-Agl(Nic), D-Orn, D-Dbu, D-Dpr or D-Orn(Nic).

In yet another aspect, the invention provides CRF antagonist peptides (including nontoxic salts thereof) having the formula:

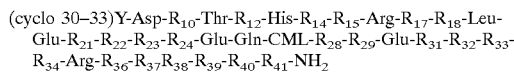

wherein Y is an acyl group having up to 15 carbon atoms; $R_{10}$, $R_{14}$, $R_{15}$, and $R_{37}$ are independently Leu or CML; $R_{12}$ is D-Phe or D-2Nal; $R_{17}$ is Glu or CML; $R_{18}$ is Val or CML; $R_{21}$ is Met or Nle; $R_{22}$, $R_{28}$, and $R_{31}$ are independently either Ala or Aib; $R_{23}$ is Arg or Lys; $R_{24}$ is Ala, Aib or CML; $R_{29}$ is Gln or Aib; $R_{32}$ is His, Aib, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{34}$ is Asn or Aib; $R_{36}$ is Lys or CML; $R_{38}$ is Met, Nle or CML; $R_{39}$ is Glu or Aib; and $R_{40}$ is Ile, CML or Aib; $R_{41}$ is Leu, CML or Aib; and wherein at least one of $R_{22}$, $R_{24}$, $R_{28}$, and $R_{31}$ is Aib. Specific analogs of this group which are considered to be particularly biopotent from the standpoint of reducing high ACTH levels and raising blood pressure are:

cyclo(30–33)[Ac-Asp$^9$, D-Phe$^{12}$, Nle$^{21,38}$, Aib$^{24}$, CML$^{27,40}$, Glu$^{30}$, Lys$^{33}$]r/hCRF(9–41);

cyclo(30–33)[Ac-Asp$^9$, D-Phe$^{12}$, Nle$^{21,38}$, Aib$^{22}$, CML$^{27,40}$, Glu$^{30}$, Lys$^{33}$]r/hCRF(9–41);

cyclo(30–33)[Ac-Asp$^9$, D-Phe$^{12}$, Nle$^{21,38}$, CML$^{27}$, Aib$^{28}$, Glu$^{30}$, Lys$^{33}$]r/hCRF(9–41);

cyclo(30–33)[Ac-Asp$^9$, D-Phe$^{12}$, Nle$^{21,38}$, CML$^{27,40}$, Aib$^{28}$, Glu$^{30}$, Lys$^{33}$]r/hCRF(9–41);

cyclo(30–33)[Ac-Asp$^9$, D-Phe$^{12}$, Nle$^{21,38}$, CML$^{27,37}$, Aib$^{28,31}$, Glu$^{30}$, Lys$^{33}$]r/hCRF(9–41);

cyclo(30–33)[Ac-Asp$^9$, D-Phe$^{12}$, Nle$^{21,38}$, CML$^{27,40}$, Glu$^{30}$, Aib$^{32}$, Lys$^{33}$]r/hCRF(9–41); and cyclo(30–33)[Ac-Asp$^9$, D-Phe$^{12}$, CML$^{14,27}$, Nle$^{21,38}$, Glu$^{30}$, Aib$^{31}$, Lys$^{33}$]r/hCRF(9–41).

The peptides of the invention may be synthesized by classical peptide solution synthesis, and such synthesis is preferred for large quantities. To obtain limited quantities, e.g. less than 1 kg, it may be preferable to prepare them using solid phase synthesis, such as that described by Merrifield, *J. Am. Chem. Soc.*, 85, p 2149 (1964), which facilitates the CRF antagonist peptides being prepared in a straightforward manner and then quickly tested to determine biological activity.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

For example, chemical synthesis of a peptide analog from one preferred group may include the initial formation of an intermediate of the following amino acid sequence: $X^1$-Asp($X^5$)-Leu-Thr($X^2$)-D-Phe-$R_{13}$($X^7$ or $X^5$)-Leu-Leu-Arg($X^3$)-$R_{17}$($X^5$)-$R_{18}$-Leu-$R_{20}$($X^5$ or $X^8$)-Nle-$R_{22}$($X^2$ or $X^5$)-$R_{23}$($X^3$, $X^6$ or $X^8$)-$R_{24}$-$R_{25}$($X^5$)-$R_{26}$($X^4$ or $X^6$)-CML-$R_{28}$-$R_{29}$($X^4$ or $X^5$)-$R_{30}$($X^5$ or $X^8$)-$R_{31}$-$R_{32}$($X^3$ or $X^7$)-$R_{33}$($X^6$ or $X^8$)-$R_{34}$($X^4$)-Arg($X^3$)-$R_{36}$($X^3$ or $X^6$)-$R_{37}$($X^7$)-Nle-$R_{39}$($X^5$)-$R_{40}$($X^2$, $X^4$ or $X^5$)-$R_{41}$($X^4$)-$X^9$ wherein: the R-groups are as hereinbefore defined.

$X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl (For), acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl methyloxycarbonyl (Fmoc), cyclopentyloxy-carbonyl, adamantyloxycarbonyl, and cyclohexyloxy-carbonyl; and (5) thiourethan-type protecting groups, such as phenylthiocarbonyl. The two preferred alpha-amino protecting groups are BOC and Fmoc.

$X^2$ is a protecting group for the hydroxyl group of Thr or Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

$X^4$ is hydrogen or a protecting group, preferably xanthyl (Xan), for the amido group of Asn or Gln. Asn or Gln is often coupled without side chain protection in the presence of hydroxybenzotriazole (HOBt).

$X^5$ is hydrogen or an ester-forming protecting group for the β- or γ-carboxyl group of Asp or Glu, preferably selected from the esters of cyclohexyl (OChx) benzyl (OBzl), 2,6-dichlorobenzyl, methyl, ethyl and t-butyl (Ot-Bu). OChx is preferred for a BOC strategy.

$X^6$ is hydrogen or a protecting group for the side chain amino substituent of Lys or Orn. Illustrative of suitable side chain amino-protecting groups are Z, 2-chlorobenzyloxycarbonyl(2Cl-Z), Tos, t-amyloxycarbonyl(Aoc), BOC and aromatic or aliphatic urethan-type protecting groups as specified hereinbefore. 2Cl-Z is preferred for a BOC strategy.

When His is present, $X^7$ is hydrogen or a protecting group for the imidazole nitrogen such as Tos or 2,4-dinitrophenyl (DNP), and when Tyr is present, $X^7$ is hydrogen or a protecting group for the hydroxyl group such as DCB. When Met is present, the sulfur may be protected, if desired, with oxygen.

$X^8$ is a protecting group for an amino side chain which is removable without simultaneously removing the protecting group $X^6$, e.g. a base-labile group such as Fmoc; or a suitable labile protecting group for a carboxyl side chain which is removable without simultaneously removing the protecting group $X^5$, e.g., a base-labile group such as OFm (fluorenylmethyl ester).

The selection of a side chain amino protecting group is not critical except that it should be one which is not removed during deprotection of the alpha-amino groups during the synthesis. Hence, the alpha-amino protecting group and the side chain amino protecting group cannot be the same.

$X^9$ is $NH_2$, a protecting group, such as an ester, or an anchoring bond used in solid phase synthesis for linking to a solid resin support, preferably one of the following:
—NH-benzhydrylamine (BHA) resin support and
—NH-paramethylbenzhydrylamine(MBHA) resin support.

Cleavage from a BHA or MBHA resin directly gives the CRF analog amide. By employing a methyl-derivative of such a resin, a methyl-substituted amide can be created, which is considered to be the equivalent of the unsubstituted amide. In the amino acid sequence for the intermediate, at least one of $X^1$, $X^2$, $X^3$, $X^4$, $X^5$, $X^6$, $X^7$ and $X^8$ is a protecting group or $X^9$ includes resin support.

For the acylated N-terminus, an acyl group having 15 carbon atoms or less is present, preferably 12 or less, as represented by Y; acetyl(Ac), formyl(For), acrylyl(Acr) and benzoyl(Bz) are the preferred acyl groups although to facilitate labeling, an acylating agent containing a hydroxy aryl moiety, such as 4-hydroxy-phenylpropionic acid (desNH$_2$-Tyr) or 4-hydroxy-phenylacetic acid, may be used. Also, Y may alternatively be a suitable sugar or lipid, which are equivalents that may be used to adjust hydrophilicity.

Thus, in one aspect, there is also provided a process for the manufacture of compounds comprising (a) forming a peptide intermediate, as defined hereinbefore, having at least one protective group wherein: $X^1$, $X^2$, $X^3$, $X^4$, $X^5$, $X^6$, $X^7$ and $X^8$ are each either hydrogen or a protective group, and $X^9$ is either a protective group or an anchoring bond to resin support or $NH_2$, (b) forming a cyclizing bond, particularly if one has not already been formed, (c) removing $X^1$ and acylating the N-terminus, (d) splitting off the remaining protective groups and any anchoring bond from said peptide intermediate, (e) optionally forming a cyclizing bond at this time, and (f) if desired, converting a resulting peptide into a nontoxic addition salt thereof.

To effect an amide cyclizing linkage (lactam bridge), cyclization may be carried out while the partially protected peptide remains attached to the resin as disclosed in U.S. Pat. Nos. 5,064,939 and 5,043,322. Such a procedure effectively creates an amide cyclizing bond between the two desired side chains while other residues, such as Asp, Glu and/or Lys, in the peptide intermediate retain their side-chain protection.

When cyclizing via an amide bond between a side-chain carboxyl group of the 30-position residue and a side-chain amino group of the 33-position residue, or vice-versa which is considered to be an equivalent linkage, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 5,043,322. Preferably cyclization is accomplished by using a base-labile protecting group, e.g., OFm, for the carboxyl side-chain of the residue to be involved in the amide-bond bridge and using Fmoc as a protecting group for the amino side chain on the other residue that is to be involved. The α-amino protecting group on the residue at the N-terminus of the intermediate and all of the other side-chain protecting groups remain in place while the two base-labile groups are removed using piperidine or the like. Following such selective removal, a reaction to accomplish cyclization is carried out by treating with BOP which effects substantially complete generation of the amide bond. If 2 lactam bridges are to be incorporated in the molecule, the 30–33 bridge is preferably effected at a point in the synthesis prior to adding the 23-position residue, or a synthesis protocol such as taught in U.S. Pat. No. 5,064,939 is employed. A BOC-protecting group is removed from the N-terminus using TFA, so the N-terminus can be acylated, before the peptide is completely deprotected and cleaved from the resin using a reagent, such as HF.

A straightforward in vitro assay can be carried out using rat anterior pituitary cells in monolayer culture to determine what CRF-activity a candidate peptide will exhibit; the procedure which is used is that generally set forth in *Endocrinology*, 91, 562 (1972). The assay will show whether a candidate peptide will exhibit some activity as a CRF agonist and stimulate ACTH secretion by activating CRF receptors on such cells; in this manner its intrinsic CRF activity is measured via the use of high doses. Essentially the same in vitro assay is employed to determine whether the candidate will exhibit strong CRF antagonistic properties when administered together with a challenge dose of CRF, usually either oCRF or r/hCRF.

A candidate CRF antagonist peptide is also readily evaluated in a binding assay using a known CRF receptor, such as that described in Perrin, M., et al., *Endocrinology*, 118, 1171–1179 (1986). Such binding assays may be carried out with human CRF-R. One such representative binding assay utilizing CRF-R receptor is described in Chen, et al., *P.N.A.S.*, 90, 8967–8971 (October 1993). Because certain of the cyclic peptides of the invention, particularly those having a D-amino acid residue in position 32, exhibit high binding affinity for all known CRF receptors, when they are radioactively or otherwise suitably labelled, they are especially valuable for use in screening assays. Such assays are advantageously used to screen for potential CRF-like ligands, in peptide or other form, using such a labelled cyclic CRF antagonist with high affinity.

The following Example I sets forth a preferred method for synthesizing CRF antagonists by the solid-phase technique.

EXAMPLE I

The synthesis of the (cyclo 30–33) [Ac-Asp$^9$, D-Phe$^{12}$, Nle$^{21,38}$, CML$^{27}$, Glu$^{30}$, Lys$^{33}$]-r/hCRF(9–41) having the amino acid sequence: (cyclo 30–33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$ is conducted in a stepwise manner on about 3 grams of a MBHA hydrochloride resin, such as available from Bachem, Inc., having a substitution range of about 0.43 to 0.46 mequiv/gm resin. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | $CH_2Cl_2$ wash-80 ml. (2 times) | 1 |
| 2 | Methanol (MeOH) wash-30 ml. (2 times) | 1 |
| 3 | $CH_2Cl_2$ wash-80 ml. (3 times) | 1 |
| 4 | 50 percent TFA plus 5 percent 1,2-ethane-dithiol in $CH_2Cl_2$-70 ml. (2 times) | 12 |
| 5 | Isopropanol wash-80 ml. (2 times) | 1 |
| 6 | TEA 12.5 percent in $CH_2Cl_2$-70 ml. (2 times) | 1 |
| 7 | MeOH wash-40 ml. (2 times) | 1 |
| 8 | $CH_2Cl_2$ wash-80 ml. (3 times) | 1 |
| 9 | BOC-amino acid (3–5 molar excess in 30 ml. of either DMF or $CH_2Cl_2$, depending upon the solubility of the particular protected amino acid, (1 time) plus DCC (3–5 molar excess) in $CH_2Cl_2$ | 30–300 |

Coupling of BOC-Ile results in the substitution of about 0.35 mmol. Ile per gram of resin.

After deprotection and neutralization, the peptide chain is built step-by-step on the resin. Generally, one to two mmol. of BOC-protected amino acid in methylene chloride is used per gram of resin (e.g. a 2–5 fold excess depending on substitution of the resin), plus one equivalent of 2 molar DCC in methylene chloride, for two hours. When BOC-Arg (Tos) is being coupled, a mixture of 50% DMF and methylene chloride is used. Bzl is used as the hydroxyl side-chain protecting group for Ser. BOC-Asn(Xan) or BOC-Gln(Xan) is coupled in the presence of one equivalent of DCC and two equivalents of HOBt in a 50% mixture of DMF and methylene chloride. Either 2Cl-Z or Fmoc is used as the protecting group for the Lys side chain depending upon whether it is to be part of a lactam bridge. Tos is used to protect the guanidino group of Arg and the imidazole group of His, and the side chain carboxyl group of Glu is protected by OChx or OFm depending upon whether it is to take part in the cyclizing reaction. At the end of the synthesis, the following composition is obtained: BOC-Asp(OChx)-Leu-Thr(Bzl)-D-Phe-His(Tos)-Leu-Leu-Arg(Tos)-Glu(OChx)-Val-Leu-Glu(OChx)-Nle-Ala-Arg(Tos)-Ala-Glu(OChx)-Gln(Xan)-Leu-Ala-Gln(Xan)-Glu(OFm)-Ala-His(Tos)-Lys(Fmoc)-Asn(Xan)-Arg(Tos)-Lys(2Cl-Z)-Leu-Nle-Glu(OChx)-Ile-Ile-MBHA resin support.

Next cyclization (lactamization) of residues 30 and 33 is performed by the method referred to hereinbefore and described more fully as follows. After washes with dichloromethane(DCM) (2×) and dimethylformamide (DMF) (2×), the OFmc/Fmoc groups of Glu[30] and Lys[33], respectively, are removed by 20% piperidine in DMF (1×1 min. and 2×10 min.), followed by washing with DMF (2×), $Et_3N$ in $CH_2Cl_2$(1×) methanol(MeOH) (2×) and DCM (2×). The peptide-resin is cyclized by reaction at room temperature with threefold excess of benzotriazol-1-yl-oxy-tris(dimethylamino)phosphonium hexafluorophosphate(BOP) in presence of excess diisoproplyethylamine(DIEA) in dimethylformamide(DMF) for four hours. Other suitable reagents are well known in the art and may alternatively be used. After washing, the cyclization may be repeated if desired to assure completion. The reaction is followed by Kaiser ninhydrin test (E. Kaiser et al., "Color test for detection of free terminal amino groups in the solid-phase synthesis of peptides", *Anal Biochem* (1970) 34:595–98).

Following cyclization, the peptide-resin is treated with TFA to remove the BOC protecting group at the N-terminus. It is then reacted with acetic anhydride to acetylate the aspartic acid residue. About 2 grams is cleaved by anhydrous HF (20 mL) in the presence of anisole (0.6 mL) at 0° C. for 90 min. The crude peptide is precipitated and washed with anhydrous diethyl ether (450 mL in 3 portions), filtered, extracted from the resin with 380 mL (r portions) of 0.1% TFA in $CH_3CN/H_2O$ (60:40) and lyophilized to give the crude product.

The crude lyophilized peptide is purified by preparative reverse-phase HPLC (RP-RHPLC) on a system composed of a Waters Associates (Milford, Mass.) Prep LC 3000 System, a Waters Associate 600E System Controller, a Shimadzu SPD-6A UV Spectrophotometric variable-wavelength detector (detection was 230 nm), Waters 1000 PrepPak Module, and a Fisher (Lexington, Mass.) Recordall Series 5000 strip chart recorder (chart speed 0.25 cm/min.). Final peptide purification is carried out in two or three steps using buffers of TEAP pH 2.25, and 0.1% TFA and/or TEAP pH 6.5 and 0.1% TFA.

The crude peptide (about 0.3–1.5 gm) is first dissolved in 400 mL buffer A: triethylammonium phosphate (TEAP) (pH 2.25) (1:4 v/v), loaded on a preparative reversed phase HPLC cartridge (5×30 cm) packed in the laboratory using Waters polyethylene sleeves and frits and Vydac $C_{18}$ silica gel (The Separations Group, Hesperia, Calif.; 300 Å pore size, 15 to 20-$\mu$m particle size). The peptide is eluted using buffer B: 60% $CH_3CN$ in buffer A with a gradient from 30 to 60% B. Buffers A (triethlyammonium phosphate (TEAP), pH 2.25) and B ($CH_3CN$ in A) are pumped at a flow rate of 95 mL/min for 90 minutes. Fractions containing a total of 50–100 mL are screened under isocratic conditions (61% B), and fractions containing the compound are identified and pooled.

In the second step, the pooled fractions are diluted with 160 mL of $H_2O$ and eluted by using as buffer A: 0.1% TFA/$H_2O$ and B: 0.1% TFA in $CH_3CN/H_2O$ (60:40), with a gradient from 40 to 70% B in 90 minutes. Fractions containing a total of 30–50 mL are screened, and fractions containing the compound are pooled and lyophilized to yield the final product peptide. Purity of about 98% is confirmed by capillary zone electrophoresis (CZE), and identity is confirmed by mass spectroscopy (MS). The measured value of 3947.87 obtained using liquid secondary ion mass spectrometry (LSIMS) is in agreement with the calculated value of 3947.23.

In vitro biopotency of the product peptide is measured as follows. Rat anterior pituitary glands from male Sprague-Dawley rats are dissociated by collagenase and plated (0.16× $10^6$ cells/well in 48-well plates) in medium containing 2% fetal bovine serum (FBS). Three days after plating, the cells are washed three times with fresh medium containing 0.1% bovine serum albumin (BSA) and incubated for 1 hour. Following the 1 hour preincubation, the cells are washed once more, and the test peptides are applied in the presence of 1 nM OCRF. At the end of a 3 hour incubation period the media are collected and the level of ACTH is determined by radioimmunoassay (Diagnostic Products Corporation). The cyclic peptide product of the above described synthesis exhibits biopotency about 1.2 (0.41–4.21) times greater than Destressin, a fairly recently developed CRF antagonist which exhibits a potency many times that of the earlier laboratory "Standard" peptide, i.e. [D-Phe[12], Nle[21,38]]r/hCRF(12–41).

Administration of the peptide inhibits the secretion of ACTH and β-endorphin-like immunoactivities (β-END-LI) and exhibits especially long duration of inhibition. The in vivo assays which are employed to test these CRF antagonists use adrenalectomized (ADX) rats. Adult male Sprague Dawley rats (230–250 g) are adrenalectomized via a lombar approach under halothane anesthesia. Their diet is supplemented with 0.9% NaCl in the drinking water and with oranges. Two days prior to the experiments, the animals are equipped with jugular cannulae, as described in C. Rivier, et al., *Endocrinology*,110, 272–278 (1982). On the morning of the experiments, the iv cannulae are connected to a line filled with heparinized saline, and the rats are placed in individual buckets and left undisturbed for 2 hours. For the experiment, a first blood sample of 0.3 mL is withdrawn, the test solution is injected (in an 0.2–0.5 mL volume), and subsequent blood samples are obtained at about 15, 45, 90 and 120 minutes. The blood samples are centrifuged, and the separated plasma are kept frozen (−20° C.) until assayed for ACTH values. Plasma ACTH levels are measured as described in C. Rivier, et al. *J. Neuroscience*, 14, 1985 (1994).

As a result of in vivo testing at a level of 100 μg/kg of body weight, it is shown that, at 60 minutes time, the cyclic CRF antagonist is more effective than Destressin in reducing ACTH levels in the serum, and much more effective than the standard CRF antagonist which has now essentially run its course so levels are substantially the same as in the control animals. At 90 minutes following injection, the cyclic compound depresses the ACTH levels even further than at the 60 minute level, while Destressin is now much less effective so that ACTH levels are significantly increasing. At 120 minutes, the ACTH levels remain at about this low level for those rats treated with the cyclic compound, well below the level of those treated with Destressin which are now close to the control rats. At 150 minutes following injection, the level of ACTH is just beginning to rise back to normal, and at 180 minutes, there is still significant improvement over the control rats. It is considered to be long-lasting.

EXAMPLE II

The synthesis of Example I is repeated, substituting D-His for His$^{32}$, to produce the following peptide: (cyclo 30–33) [Ac-Asp$^9$, D-Phe$^{12}$, Nle$^{21,38}$, CML$^{27}$, Glu$^{30}$, D-His$^{32}$, Lys$^{33}$]-r/hCRF(9–41), having the formula:

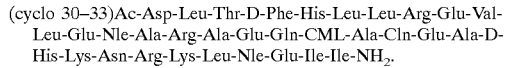
(cyclo 30–33)Ac-Asp-Leu-Thr-D-Phe-His-Leu-Leu-Arg-Glu-Val-Leu-Glu-Nle-Ala-Arg-Ala-Glu-Gln-CML-Ala-Cln-Glu-Ala-D-His-Lys-Asn-Arg-Lys-Leu-Nle-Glu-Ile-Ile-NH$_2$.

It has a purity of about 98% as a result of HPLC, which is confirmed by CZE. The measured value of 3947.2 obtained using LSIMS is in agreement with the calculated value of 3947.23. The peptide's biopotency, determined by in vitro testing as previously described, is about 2.22 (0.30–7.47) times that of Destressin. In vivo testing shows that it is very significantly more effective than Destressin at 90, 120 and 150 minutes at a dosage of about 100 μg/kg in adrenalectomized rats; it is considered to be fairly long-acting and nearly equal to Peptide I.

EXAMPLE III

The synthesis of Example I is generally repeated, substituting C$^\alpha$MeLeu for Leu$^{14}$, to produce the following peptide: (cyclo 30–33)[Ac-Asp$^9$, D-Phe$^{12}$, CML$^{14,27}$, Nle$^{21,38}$, Glu$^{30}$, Lys$^{33}$]-r/hCRF(9–41), having the formula:

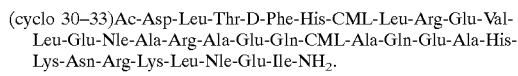
(cyclo 30–33)Ac-Asp-Leu-Thr-D-Phe-His-CML-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-NH$_2$.

It has a purity of about 98% which is confirmed by CZE. A measured value of 3961.28 is obtained using LSIMS and is in agreement with the calculated value of 3961.2.

The peptide's biopotency, determined by in vivo testing as previously described, is greater than that of Destressin at 90 and 150 minutes. It remains significantly effective at 210 minutes, continues to show bioactivity at 270 minutes, and is considered to be very long-acting in vivo.

EXAMPLE IV

The synthesis of Example I is repeated, substituting C$^\alpha$MeLeu for Val$^{18}$, to produce the following peptide: (cyclo 30–33)[Ac-Asp$^9$, D-Phe$^{12}$, CML$^{18,27}$, Nle$^{21,38}$, Glu$^{30}$, Lys$^{33}$]-r/hCRF(9–41), having the formula:

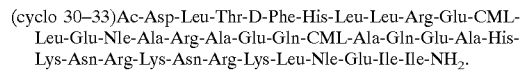
(cyclo 30–33)Ac-Asp-Leu-Thr-D-Phe-His-Leu-Leu-Arg-Glu-CML-Leu-Glu-Nle-Ala-Arg-Ala-Glu-Gln-CML-Ala-Gln-Glu-Ala-His-Lys-Asn-Arg-Lys-Asn-Arg-Lys-Leu-Nle-Glu-Ile-Ile-NH$_2$.

It has a purity of about 98% which is confirmed by CZE. The measured value of 3975.8 obtained using LSIMS is in agreement with the calculated value of 3975.3. The peptide's biopotency, determined by in vitro testing as previously described, is about 13 times that of the Standard. It is found to be very long-acting in vivo, being substantially better than Destressin at 120 minutes and remaining effective for longer than 180 minutes.

EXAMPLE V

The synthesis of Example V is repeated, substituting C$^\alpha$MeLeu for Lys$^{36}$, to produce the following peptide: (cyclo 30–33)[Ac-Asp$^9$, D-Phe$^{12}$, Nle$^{21,38}$, CML$^{27,36}$, Glu$^{30}$, Lys$^{33}$]-r/hCRF(9–41) having the formula:

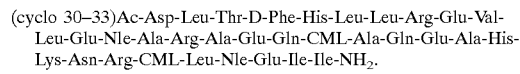
(cyclo 30–33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-CML-Leu-Nle-Glu-Ile-Ile-NH$_2$.

It has a purity of about 98% which is confirmed by CZE. The measured value of 3946.26 obtained using LSIMS is in agreement with the calculated value of 3946.24. In vivo testing at a dosage of about 100 μ/kg shows that it is more effective than Destressin at 90 minutes, and retains substantial effectiveness at 135 minutes. It is considered to be of medium duration.

EXAMPLE VI

The synthesis of Example I is repeated, substituting C$^\alpha$MeLeu for Leu$^{37}$, to produce the following peptide: (cyclo 30–33)[Ac-Asp$^9$, D-Phe$^{12}$, Nle$^{21,38}$, CML$^{27,37}$, Glu$^{30}$, Lys$^{33}$]-r/hCRF(9–41), having the formula:

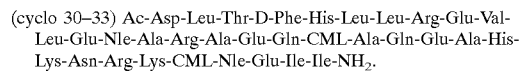
(cyclo 30–33) Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-Ile-Ile-NH$_2$.

It has a purity of about 98% which is confirmed by CZE. A measured value of 3961.20 obtained using LSIMS is in agreement with the calculated value of 3961.2. In vivo testing at a dosage of about 100 μg/kg shows that it is substantially more effective than Destressin at 90, 120, 135, 180 and 210 minutes, and that it retains significant effectiveness at 270 minutes. It is considered to be very long-acting.

EXAMPLE VII

The synthesis of Example I is repeated, substituting C$^\alpha$MeLeu for Ile$^{40}$, to produce the following peptide: (cyclo 30–33)[Ac-Asp$^9$, D-Phe$^{12}$, Nle$^{21,38}$, CML$^{27,40}$, Glu$^{30}$, Lys$^{33}$]-r/hCRF(9–41), having the formula:

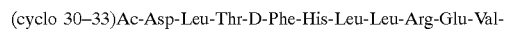
(cyclo 30–33)Ac-Asp-Leu-Thr-D-Phe-His-Leu-Leu-Arg-Glu-Val-

Leu-Glu-Nle-Ala-Arg-Ala-Glu-Gln-CML-Ala-Gln-Glu-Ala-His-Lys-Asn-Arg-Lys-Leu-Nle-Glu-CML-Ile-NH$_2$.

It has a purity of about 98% which is confirmed by CZE. A measured value of 3961.30 obtained using LSIMS is in agreement with the calculated value of 3961.2. In vivo testing by iv injection at a dosage of 100 μg/kg shows that it is substantially more effective than Destressin at 90 and 150 minutes. When administered iv at a dosage of 100 μg per rat (4 times the previous dosage), it exhibits such high effectiveness for 6 hours, and still exhibits some effectiveness at 12 hours. It is considered to be very long-acting. The peptide is also formulated in corn oil and in an aqueous 3–6% mannitol solution and is injected s.c. At a dosage of about 30 μg in corn oil and an aqueous solution dosage of 100 μg, both formulations show significant inhibition of secretion of ACTH for over 24 hours.

EXAMPLE VIII

The synthesis of Example I is repeated, substituting C$^\alpha$MeLeu for Ile$^{41}$, to produce the following peptide: (cycle 30–33)[Ac-Asp$^9$, D-Phe$^{12}$, Nle$^{21,38}$, CML$^{27,41}$, Glu$^{30}$, Lys$^{33}$]-r/hCRF(9–41), having the formula:

(cyclo 30–33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-CML-NH$_2$.

It has a purity of about 98% which is confirmed by CZE. A measured value of 3961.30 obtained using LSIMS is in agreement with the calculated value of 3961.2. In vivo testing at a dosage of about 100 μg/kg shows that it is more effective than Destressin at 90 and 120 minutes, but that it is no longer effective after 270 minutes.

EXAMPLE IX

The synthesis of Example I is repeated, substituting C$^\alpha$MeLeu for Leu$^{10}$, to produce the following peptide: (cycle 30–33)[Ac-Asp$^9$, CML$^{10,27}$, D-Phe$^{12}$, Nle$^{21,38}$, Glu$^{30}$, Lys$^{33}$]-r/hCRF(9–41), having the formula:

(cyclo 30–33)Ac-Asp-CML-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-NH$_2$.

It has a purity of about 98% which is confirmed by CZE. The measured value of 3961.3 Da obtained using LSIMS is in agreement with the calculated value of 3961.2 Da. It is found to be of medium duration in vivo, being substantially better than Destressin at 90 and 150 minutes, but remaining barely active at 210 minutes at a dosage of about 100 μg/kg.

EXAMPLE X

The synthesis of Example I is repeated, substituting C$^\alpha$MeLeu for Leu$^{15}$, to produce the following peptide: (cyclo 30–33)[Ac-Asp$^9$, D-Phe$^{12}$, CML$^{15,27}$, Nle$^{21,38}$, Glu$^{30}$, Lys$^{33}$]-r/hCRF(9–41), having the formula:

(cyclo 30–33)Ac-Asp-Leu-Thr-D-Phe-His-Leu-CML-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. The measured value of 3961.3 Da obtained using LSIMS is in agreement with the calculated value of 3961.2 Da. It is found to be short-acting in vivo, being somewhat better than Destressin at 90 minutes, but then losing effectiveness fairly rapidly so as to be only slightly effective at 150 minutes at a dosage of about 100 μg/kg.

EXAMPLE XI

The synthesis of Example XI is repeated, substituting C$^\alpha$MeLeu for Leu$^{19}$, to produce the following peptide: (cyclo 30–33)[Ac-Asp$^9$, D-Phe$^{12}$, CML$^{19,27}$, Nle$^{21,38}$, Glu$^{30}$, Lys$^{33}$]-r/hCRF(9–41), having the formula:

(cyclo 30–33)Ac-Asp-Leu-Thr-D-Phe-His-Leu-Leu-Arg-Glu-Val-CML-Glu-Nle-Ala-Arg-Ala-Glu-Glu-Gln-CML-Ala-Gln-Glu-Ala-D-His-Lys-Asn--Arg-Lys-Leu-Nle-Glu-Ile-Ile-NH$_2$.

It has a purity of about 98% which is confirmed by CZE. The measured value of 3961.3 Da obtained using LSIMS is in agreement with the calculated value of 3961.2 Da. In vivo testing shows that it is more effective than Destressin at 90 minutes. It still exhibits effectiveness at 150 minutes but not at 210 minutes at a dosage of about 100 μg/kg. It is considered to be generally equivalent to Peptide I.

EXAMPLE XII

The synthesis of Example I is repeated, substituting C$^\alpha$MeLeu for Ala$^{24}$, to produce the following peptide: (cyclo 30–33)[Ac-Asp$^9$, D-Phe$^{12}$, Nle$^{21,38}$, CML$^{24,27}$, Glu$^{30}$, Lys$^{33}$]-r/hCRF(9–41), having the formula:

(cyclo 30–33)Ac-Asp-Leu-Thr-D-Phe-His-Leu-Leu-Arg-Glu-Val-Leu-Glu-Nle-Ala-Arg-CML-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. The measured value of 4003.3 Da obtained using LSIMS is in agreement with the calculated value of 4003.3 Da. It is found to have medium duration of in vivo activity, being substantially better than Destressin at 90 and 150 minutes, but losing effectiveness at about 210 minutes at a dosage of about 100 μg/kg.

EXAMPLE XIII

The synthesis of Example I is generally repeated, substituting C$^\alpha$MeLeu for Leu$^{14}$, and Ile$^{40}$ to produce the following peptide: (cyclo 30–33)[Ac-Asp$^9$, D-Phe$^{12}$, CML$^{14,27,37,40}$, Nle$^{21,38}$, Glu$^{30}$, Lys$^{33}$]-r/hCRF(9–41), having the formula:

(cyclo 30–33)Ac-Asp-Leu-Thr-D-Phe-His-CML-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-CML-Ile-NH$_2$.

It has a purity of about 98% which is confirmed by CZE. Using LSIMS, a measured value is obtained that is in agreement with the calculated value. The peptide is effective to inhibit the secretion of ACTH.

EXAMPLE XIII A

The synthesis of Example XIII is repeated, substituting D-2Nal for D-Phe$^{12}$, to produce the following peptide: (cyclo 30–33)[Ac-Asp$^9$, D-2Nal$^{12}$, CML$^{14,27,37,40}$, Nle$^{21,38}$, Glu$^{30}$, Lys$^{33}$]-r/hCRF(9–41), having the formula:

(cyclo 30–33)Ac-Asp-Leu-Thr-D-2Nal-His-CML-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-CML-Ile-NH$_2$.

It has a purity of about 98% which is confirmed by CZE. Using LSIMS, a measured value is obtained that is in agreement with the calculated value. The peptide is effective to inhibit the secretion of ACTH.

EXAMPLE XIII B

The synthesis of Example I is repeated, substituting C$^\alpha$MeLeu for Leu$^{37}$ and Ile$^{40}$, to produce the following peptide: (cyclo 30–33)[Ac-Asp$^9$, D-Phe$^{12}$, Nle$^{21,38}$, CML$^{27,37,40}$, Glu$^{30}$, Lys$^{33}$]-r/hCRF(9–41), having the formula:

(cyclo 30–33)Ac-Asp-Leu-Thr-D-Phe-His-Leu-Leu-Arg-Glu-Val-Leu-Glu-Nle-Ala-Arg-Ala-Ala-Glu-Gln-CML-Ala-Gln-Glu-Ala-His-Lys-Asn-Arg-Lys-CML-Nle-Glu-CML-Ile-NH$_2$.

It has a purity of about 98% which is confirmed by CZE. The peptide is effective to inhibit the secretion of ACTH.

EXAMPLE XIII C

The synthesis of Example I is repeated, substituting C$^\alpha$MeLeu for Glu$^{17}$, to produce the following peptide: (cyclo 30–33)[Ac-Asp$^9$, D-Phe$^{12}$, CML$^{17,27}$, Nle$^{21,38}$, Glu$^{30}$, Lys$^{33}$]-r/hCRF(9–41), having the formula:

(cyclo 30–33)Ac-Asp-Leu-Thr-D-Phe-His-Leu-Leu-Arg-CML-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. The synthesis is repeated substituting BOC-D-2Nal for BOC-D-Phe to produce the peptide (cyclo 30–33)[Ac-Asp$^9$, D-2Nal$^{12}$, CML$^{17,27}$, Nle$^{21,38}$, Glu$^{30}$, Lys$^{33}$]r/hCRF(9–41). HPLC shows a purity of about 98% which is confirmed by CZE.

Both peptides have measured MS values in agreement with the calculated values and are effective in vivo to inhibit the secretion of ACTH.

EXAMPLE XIII D

The synthesis of Example I is generally repeated, substituting C$^\alpha$MeLeu for Leu$^{15}$ and Aib for His$^{32}$, to produce the following peptide: (cyclo 30–33)[Ac-Asp$^9$, D-Phe$^{12}$, CML$^{15,27}$, Nle$^{21,38}$, Glu$^{30}$,Aib$^{32}$, Lys$^{33}$]-r/hCRF(9–41), having the formula:

(cyclo 30–33)Ac-Asp-Leu-Thr-D-Phe-His-Leu-CML-Arg-Glu-Val-Leu-Glu-Nle-Ala-Arg-Ala-Glu-Gln-CML-Ala-Gln-Glu-Ala-Aib-Lys-Asn-Arg-Lys-Leu-Nle-Glu-Ile-Ile-NH$_2$.

It has a purity of about 98% and is effective to inhibit the secretion of ACTH.

EXAMPLE XIII E

The synthesis of Example I is repeated, substituting C$^\alpha$MeLeu for Nle$^{21}$ and Aib for His$^{32}$, to produce the following peptide: (cyclo 30–33)[Ac-Asp$^9$, D-Phe$^{12}$, CML$^{21,27}$, Glu$^{30}$, Aib$^{32}$, Lys$^{33}$, Nle$^{38}$]-r/hCRF(9–41), having the formula:

(cyclo 30–33)Ac-Asp-Leu-Thr-D-Phe-His-Leu-Leu-Arg-Glu-Val-Leu-Glu-CML-Ala-Arg-Ala-Glu-Gln-CML-Ala-Gln-Glu-Ala-Aib-Lys-Asn-Arg-Lys-Leu-Nle-Glu-Ile-Ile-NH$_2$.

The peptide is effective to inhibit the secretion of ACTH.

EXAMPLE XIII F

The synthesis of Example I is repeated, substituting C$^\alpha$MeLeu for Nle$^{38}$, to produce the following peptide: (cyclo 30–33)[Ac-Asp$^9$, D-Phe$^{12}$, Nle$^{21}$, CML$^{27,38}$, Glu$^{30}$, Lys$^{33}$-r/hCRF(9–41), having the formula:

(cyclo 30–33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-CML-Glu-Ile-Ile-NH$_2$.

It has a purity of about 98% which is confirmed by CZE. A measured value of 3961.28 obtained using LSIMS is in agreement with the calculated value of 3961.2. The peptide's biopotency, determined by in vitro testing as previously described, is about 1.4 times the Standard, and it is considered effective to inhibit the secretion of ACTH in vivo.

EXAMPLE XIII G

The synthesis of Example I is generally repeated, substituting C$^\alpha$MeLeu for Leu$^{40}$ and Aib for His$^{32}$, to produce the following peptide: (cyclo 30–33)[Ac-Asp$^9$, D-Phe$^{12}$, Nle$^{21,38}$, CML$^{27,40}$, Glu$^{30}$, Aib$^{32}$, Lys$^{33}$]r/hCRF(9–41), having the formula:

(cyclo 30–33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-Aib-Lys-Asn-Arg-Lys-Leu-Nle-Glu-CML-Ile-NH$_2$.

It has a purity of about 98%. Using LSIMS, a measured value is obtained that is in agreement with the calculated value. Based upon a single test, it appears to be effective to inhibit the secretion of ACTH for a period of time which is longer than that of the peptide of Example VII.

EXAMPLE XIII H

The synthesis of Example I is repeated a number of times, each time also making at least one additional substitution of CML for a different residue. As a result, the following (cyclo 30–33) cyclic peptides are produced:

[Ac-Asp$^9$, D-Phe$^{12}$, CML$^{18,27}$, Nle$^{21,38}$, Glu$^{30}$, D-His$^{32}$, Lys$^{33}$]-r/hCRF(9–41);

[Ac-Asp$^9$, D-Phe$^{12}$, Nle$^{21,38}$, CML$^{27,36,40}$, Glu$^{30}$, Lys$^{33}$]-r/hCRF(9–41);

[Ac-Asp$^9$, D-Phe$^{12}$, Nle$^{21,38}$, CML$^{27,40}$, Glu$^{30}$, D-His$^{32}$, Lys$^{33}$]-r/hCRF(9–41);

[Ac-Asp$^9$, D-Phe$^{12}$, Nle$^{21,38}$, CML$^{27,36,37}$, Glu$^{30}$, Lys$^{33}$]-r/hCRF(9–41);

[Ac-Asp$^9$, D-Phe$^{12}$, Nle$^{21,38}$, CML$^{27,37,41}$, Glu$^{30}$, Lys$^{33}$]-r/hCRF(9–41);

[Ac-Asp$^9$, D-Phe$^{12}$, Nle$^{21,38}$, CML$^{27,37,41}$, Glu$^{30}$, D-His$^{32}$, Lys$^{33}$]-r/hCRF(9–41);

[Ac-Asp$^9$, D-Phe$^{12}$, Nle$^{21,38}$, CML$^{27,36,40}$, Glu$^{30}$, D-His$^{32}$, Lys$^{33}$]-r/hCRF(9–41); and

[Ac-Asp$^9$, D-Phe$^{12}$, CML$^{14,27,40}$, Nle$^{21,38}$, Glu$^{30}$, Lys$^{33}$]-r/hCRF(9–41).

Administration of these peptides stimulates the secretion of ACTH and β-END-LI, and iv injection lowers blood pressure.

EXAMPLE XIV

The synthesis of (cyclo 30–33) [Ac-Asp$^9$, D-Phe$^{12}$, Nle$^{21,38}$, CML$^{27}$, Glu$^{30}$, Orn$^{33}$]-r/hCRF(9–41) having the amino acid sequence: (cyclo 30–33)Ac-Asp-Leu-Thr-D-Phe-His-Leu-Arg-Glu-Val-Leu-Glu-Nle-Ala-Arg-Ala-Glu-Gln-CML-Ala-Gln-Glu-Ala-His-Orn-Asn-Arg-Lys-Leu-Nle-Glu-Ile-Ile-NH$_2$ is conducted as described in Example I above, except that residue 33 is Orn instead of Lys. Administration of the peptide inhibits the secretion of ACTH and β-END-LI.

EXAMPLE XIV A

The synthesis of (cyclo 30–33) [Ac-Asp$^9$, D-Phe$^{12}$, Nle$^{21,38}$, CML$^{27,40}$, Glu$^{30}$, Aib$^{32}$, Orn$^{33}$]-r/hCRF(9–41) having the amino acid sequence: (cyclo 30–33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-Aib-Orn-Asn-Arg-Lys-Leu-Nle-Glu-CML-Ile-NH$_2$ is conducted as described in Example XIV, except that residue 40 is CML instead of Leu and residue 32 is Aib instead of His. Administration of the peptide inhibits the secretion of ACTH and β-END-LI.

EXAMPLE XIV B

The peptide (cyclo 30–33) [Ac-Asp$^9$, D-Phe$^{12}$, Nle$^{18,21}$, CML$^{27,40}$, Glu$^{30}$, D-His$^{32}$, Lys$^{33}$]-Carp Urotensin I(9–41) having the formula:

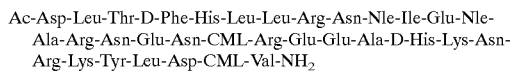

is synthesized. Testing in accordance with the general procedure set forth in Example I shows that the cyclic compound inhibits the secretion of ACTH and β-END-LI.

EXAMPLE XIV C

The peptide (cyclo 29–32) [Ac-Asp$^8$, D-Leu$^{11}$, Nle$^{17}$, CML$^{26,39}$, Glu$^{29}$, D-His$^{31}$1, Lys$^{32}$]-sauvagine(8–40) having the formula:

Ac-Asp-Leu-Ser-D-Leu-Glu-Leu-Leu-Arg-Lys-Nle-Ile-Glu-Ile-Glu-Lys-Gln-Glu-Lys-CML-Lys-Gln-Glu-Ala-D-His-Lys-Asn-Arg-Leu-Leu-Leu-Asp-CML-Ile-NH$_2$ is synthesized. Testing in accordance with the general procedure set forth in Example I shows that the cyclic compound inhibits the secretion of ACTH and β-END-LI.

The synthesis is repeated to yield the peptide: (cyclo 29–32) [Ac-Asp$^8$, D-Leu$^{11}$, Nle$^{17}$, CML$^{26,39}$, Glu$^{29}$, Aib$^{31}$, Lys$^{32}$]-Sauvagine (8–40). The peptide is biopotent in inhibiting the secretion of ACTH.

EXAMPLE XIV D

The peptide (cyclo 30–33)[Ac-Asp$^9$, D-Phe$^{12}$, CML$^{27,40}$, Glu$^{30}$, Aib$^{32}$, Lys$^{33}$]-α-helical CRF(9–41) having the formula:

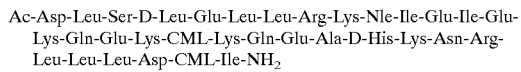

is synthesized.

Testing in accordance with the general procedure set forth in Example I shows that the cyclic compound inhibits the secretion of ACTH and β-END-LI.

EXAMPLE XIV E

The peptide (cyclo 30–33)[Ac-Asp$^9$, D-Phe$^{12}$, Nle$^{18,21}$1, CML$^{27,40}$, Glu$^{30}$, Aib$^{32}$, Lys$^{33}$]-Sucker Urotensin I(9–41) having the formula:

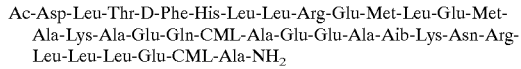

is synthesized. The peptide is biopotent to inhibit the secretion of ACTH and β-END-LI.

EXAMPLE XIV F

The peptide (cyclo 29–32)[Ac-Asp$^8$, D-Leu$^{11}$, Nle$^{17}$, CML$^{26}$, Glu$^{29}$, Aib$^{31}$, Lys$^{32}$]-sauvagine(8–40) having the formula:

Ac-Asp-Leu-Ser-D-Leu-Glu-Leu-Leu-Arg-Lys-Nle-Ile-Glu-Ile-Glu-Lys-Gln-Glu-Lys-CML-Lys-Gln-Glu-Ala-Aib-Lys-Asn-Arg-Leu-Leu-Leu-Asp-Thr-Ile-NH$_2$ is synthesized. The peptide is biopotent to inhibit the secretion of ACTH and β-END-LI.

EXAMPLE XV

The synthesis of Example XIII is repeated a number of times, each time also making one or more substitutions of Aib and/or CML for residues in that CRF antagonist peptide. As a result, the following (cyclo 30–33) cyclic peptides are produced:

[Ac-Asp$^9$, D-Phe$^{12}$, Nle$^{21,38}$, Aib$^{22}$, CML$^{27}$, Glu$^{30}$, Lys$^{33}$]-r/hCRF (9–41);
[Ac-Asp$^9$, D-Phe$^{12}$, Nle$^{21,38}$, Aib$^{24}$, CML$^{27}$, Glu$^{30}$, Lys$^{33}$]-r/hCRF (9–41);
[Ac-Asp$^9$, D-Phe$^{12}$, Nle$^{21,38}$, CML$^{27}$, Aib$^{28}$, Glu$^{30}$, Lys$^{33}$]-r/hCRF (9–41);
[Ac-Asp$^9$, D-Phe$^{12}$, Nle$^{21,38}$, CML$^{27}$, Aib$^{29}$, Glu$^{30}$, Lys$^{33}$]-r/hCRF (9–41);
[Ac-Asp$^9$, D-Phe$^{12}$, Nle$^{21,38}$, CML$^{27}$, Glu$^{30}$, Aib$^{31}$, Lys$^{33}$]-r/hCRF (9–41);
[Ac-Asp$^9$, D-Phe$^{12}$, Nle$^{21,38}$, CML$^{27}$, Glu$^{30}$, Lys$^{33}$, Aib$^{34}$]-r/hCRF (9–41);
[Ac-Asp$^9$, D-Phe$^{12}$, Nle$^{21,38}$, CML$^{27}$, Glu$^{30}$, Lys$^{33}$, Aib$^{39}$]-r/hCRF (9–41);
[Ac-Asp$^9$, D-Phe$^{12}$, Nle$^{21,38}$, CML$^{27}$, Glu$^{30}$, Lys$^{33}$, Aib$^{40}$]-r/hCRF (9–41);
[Ac-Asp$^9$, D-Phe$^{12}$, Nle$^{21,38}$, CML$^{27}$, Glu$^{30}$, Lys$^{33}$, Aib$^{41}$]-r/hCRF (9–41);
[Ac-Asp$^9$, D-Phe$^{12}$, Nle$^{21,38}$, CML$^{27,40}$, Glu$^{30}$, LyS$^{33}$, Aib$^{41}$]-r/hCRF(9–41);
[Ac-Asp$^9$, D-Phe$^{12}$, Nle$^{21,38}$, Aib$^{22}$, CML$^{27,40}$, Glu$^{30}$, Lys$^{33}$]-r/hCRF(9–41);
[Ac-Asp$^9$, D-Phe$^{12}$, Nle$^{21,38}$, Aib$^{24}$, CML$^{27,40}$, Glu$^{30}$, Lys$^{33}$]-r/hCRF(9–41);
[Ac-Asp$^9$, D-Phe$^{12}$, Nle$^{21,38}$, Aib$^{22,24}$, CML$^{27}$, Glu$^{30}$, Lys$^{33}$]-r/hCRF(9–41);
[Ac-Asp$^9$, D-Phe$^{12}$, Nle$^{21,38}$, CML$^{27,40}$, Aib$^{28}$, GlU$^{30}$, Lys$^{33}$]-r/hCRF(9–41);
[Ac-Asp$^9$, D-Phe$^{12}$, Nle$^{21,38}$, CML$^{27}$, Glu$^{30}$, Aib$^{31,41}$, Lys$^{33}$]-r/hCRF(9–41);
[Ac-Asp$^9$, D-Phe$^{12}$, CML$^{14,27}$, Nle$^{21,38}$, Glu$^{30}$, Aib$^{31}$, Lys$^{33}$]-r/hCRF(9–41);
[Ac-Asp$^9$, D-Phe$^{12}$, Nle$^{21,38}$, CML$^{27,40}$, Aib$^{32,41}$, Glu$^{30}$, Lys$^{33}$]-r/hCRF(9–41); and
[Ac-Asp$^9$, D-Phe$^{12}$, CML$^{14,27}$, Nle$^{21,38}$, Aib$^{24,41}$, Glu$^{30}$, Lys$^{33}$]-r/hCRF(9–41).

Administration of these peptides stimulates the secretion of ACTH and β-END-LI, and iv injection lowers blood pressure.

EXAMPLE XVI

Using the procedure as generally set forth in Example I, the following CRF antagonist peptides are also prepared:
(c 30–33) [Ac-Asp$^9$, CML$^{17,27}$, Glu$^{30}$, Lys$^{33}$]-AHC(9–41);
" [Ac-Asp$^9$, CML$^{14,27}$, Lys$^{28,33}$, Glu$^{30}$]-oCRF(9–41);
" [Acr-Asp$^9$, Ser$^{11}$, D-Phe12, CML$^{14,27}$, Nle$^{21,38}$, Glu$^{30}$, Lys$^{33}$]-r/hCRF(9–41);
" [Bz-Asp$^9$, D-2Nal$^{12}$, CML$^{14,27}$, Glu$^{30}$, Lys$^{33}$]-oCRF (9–41);
" [Pn-Asp$^9$, CML$^{17,27}$, Nle$^{18,21}$, Glu$^{30}$, Lys$^{33}$]-AHC(9–41);
" [Acr-Asp$^9$, D-Leu$^{12}$, CML$^{17,27}$, Glu$^{30}$, Lys$^{33}$]-r/hCRF (9–41);
" [Bt-Asp$^9$, D-Phe$^{12}$, CML$^{27,37}$, Nle$^{21}$, Glu$^{30}$, Lys$^{33}$]-oCRF (9–41);
" [Acr-Asp$^9$, D-4ClPhe$^{12}$, CML$^{15,27}$, Glu$^{30}$, Lys$^{33}$]-AHC (9–41);
" [Nph-Asp$^9$, D-Phe$^{12}$, CML$^{15,27}$, Nle$^{21,38}$, Arg$^{28}$, Glu$^{30}$, Lys$^{33}$]-r/hCRF(9–41);

(c 30–33) [Bz-Asp$^9$, D-Phe$^{12}$, CML$^{14,27}$, Nle$^{21,38}$, Glu$^{30}$, D-Trp$^{32}$, Lys$^{33}$]-r/hCRF(9–41);
" [Vac-Asp$^9$, D-Phe$^{12}$, CML$^{27,37}$, Nle$^{21,38}$, Glu$^{30}$, Lys$^{33}$]-r/hCRF(9–41);
" [iPn-Asp$^9$, Nle$^{18,21}$, CML$^{27,37}$, Glu$^{30}$, D-His$^{32}$, Lys$^{33}$]-AHC(9–41);
" [Nph-Asp$^9$, D-Phe$^{12}$, CML$^{27,37}$, Glu$^{30}$, D-Trp$^{32}$, Lys$^{33}$, Aib$^{28}$]-r/hCRF(9–41);
" [Bz-Asp$^9$, CML$^{27,37}$, Nle$^{21,38}$, Glu$^{30}$, Lys$^{33}$]-r/hCRF(9–41);
" [For-Asp$^9$, D-Phe$^{12}$, CML$^{14,27}$, Glu$^{30}$, Aib$^{32}$, Lys$^{33}$]-r/hCRF (9–41);
" [For-Asp$^9$, D-Pal$^{12}$, Nle$^{21}$, CML$^{27,38}$, Glu$^{30}$, Lys$^{33}$]-oCRF(9–41);
" [Bt-Asp$^9$, D-Tyr-Asp$^9$, D-Phe$^{12}$, CML$^{27}$, Glu$^{30}$, Lys$^{33}$]-AHC(9–41);
" [Vl-Asp$^9$, D-Phe$^{12}$, CML$^{14,27}$, Nle$^{21,38}$, Lys$^{28,33}$, Glu$^{30}$]-r/hCRF(9–41);
" [Flu-Asp$^9$, Ser$^{11}$, D-Phe$^{12}$, Nle$^{21,38}$, CML$^{27,40}$, Glu$^{30}$, Aib$^{32}$, Lys$^{33}$]-r/hCRF(9–41);
" [Ac-Asp$^9$, D-Phe$^{12}$, Nle$^{21,38}$, Lys$^{23}$, CML$^{27,41}$, Glu$^{30}$, Aib$^{32}$, Lys$^{33}$]-r/hCRF(9–41);
" [Ac-Asp$^9$, D-2Nal$^{12}$, CML$^{14,27}$, Glu$^{30}$, D-2Nal$^{32}$, Lys$^{33}$]-oCRF(9–41);
" [Acr-Asp$^9$, CML$^{17,27}$, Nle$^{18,21}$, Glu$^{30}$, D-Arg$^{32}$, Lys$^{33}$]-AHC(9–41);
" [Bz-Asp$^9$, D-Phe$^{12}$, CML$^{27}$, Glu$^{30}$, D-Leu$^{32}$, Lys$^{33}$]-r/hCRF(9–41);
" [Ac-Asp$^9$, D-Phe$^{12}$, CML$^{27,37}$, Nle$^{21}$, Glu$^{30}$, Tyr$^{32}$, Lys$^{33}$]-oCRF(9–41); and
" [Nph-Asp$^9$, D-4Cpa$^{12}$, CML$^{27}$, Glu$^{30}$, Arg$^{32}$, Lys$^{33}$]-AHC(9–41)

These peptides are biopotent in inhibiting the secretion of ACTH and β-END-LI in response to various stimuli.

Preferably the cyclic CRF antagonist does not inherently activate the CRF receptor. Generally a peptide is considered not to significantly activate the CRF receptor when its intrinsic activity measures about 20% or less of the native compound. Preferred antagonists have an intrinsic activity of about 15% or less; however, intrinsic activity is simply one factor to be balanced against a peptide's potency as an antagonist.

CRF profoundly stimulates the pituitary-adrenalcortical axis, and CRF antagonists are useful to inhibit the functions of this axis in certain types of patients experiencing high ACTH and endogenous glucocorticoid production. For example, CRF antagonists may be useful in regulating pituitary-adrenal function in patients having pituitary Cushings disease or any CRF-sensitive tumor. Preferred members of the improved CRF antagonists provided by the invention bind with high affinity to CRF receptors without significantly activating the receptors, i.e. they exhibit an intrinsic activity or agonism less than 15% of that of ovine CRF. Moreover, they are considered to have a neuronal effect when administered peripherally, e.g. iv, s.c., intranasally, intrapulmonarily, etc., and may be used to combat stress-induced stomach disorders which result from acid secretion.

Most other regulatory peptides have been found to have effects upon the endocrine system, the central nervous system and upon the gastrointestinal tract. Because ACTH and β-END-LI secretion is the "sine qua non" of mammal's response to stress, it is not surprising that CRF has significant effects on the brain as a mediator of many of the body's stress responses. Accordingly, CRF antagonists delivered to the brain should also find application in modifying the mood, learning and behavior, e.g. drug addition and drug and alcohol withdrawal, of normal and mentally disordered individuals. Furthermore, CRF antagonists in the brain should ameliorate stress-induced conditions to which endogenous CRF might contribute, including some types of hypertension, anorexia nervosa, hemorrhagic stress, infertility, decreased libido, impotency and hyperglycemia. Because peripherally administered CRF antagonists reduce the levels of ACTH, β-END, β-lipotropin, other pro-opiomelanocortin gene products and corticosterone, administration of the antagonists may be used to reduce the effects of all of these substances on the brain to thereby influence memory, mood, pain appreciation, etc., and more specifically, alertness, depression and/or anxiety, as well as to modulate the immune system, gastrointestinal tract and adrenalcortical growth and function. They may also be used to treat HIV infections and Alzheimer's disease.

Because CRF antagonists will block the hypothalamic pituitary axis (HPA) and therefore block ACTH and corticosterone secretion in instances when the desired effects of administration may be on other functions (e.g. immune, neuronal, etc.), hormonal replacement therapy (i.e. administration of ACTH and/or corticosterone) may be advisable as an adjunct to CRF antagonist therapy, as necessary to maintain homeostasis. As a parallel example, testosterone replacement is often used when treating normal humans with GnRH antagonists for male contraception in order to retain libido. Such hormonal replacement is not indicated in the case of treatment of prostate cancer.

All CRF-related peptides have been shown to dilate the mesenteric vascular bed. CRF antagonists should also be of use for decreasing blood flow to the gastrointestinal tract of mammals, particularly humans. Also, because CRF influences gastric acid production, CRF antagonists should also be effective to modulate gastrointestinal functions, including abdominal bowel syndrome and inflammatory diseases.

CRF antagonists or the nontoxic addition salts thereof, combined with a pharmaceutically acceptable carrier to form a pharmaceutical composition, may be administered to mammals, including humans, either intravenously, subcutaneously, intramuscularly, intrapulmonarily, percutaneously, e.g. intranasally, intracerebroventricularly or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to inhibit endogenous glucocorticoid production or for possible uses outlined above. Administration may be in a variety of dosage forms such as tablets, lozenges, powders, syrups, injectable solutions, injectable depot formulations and the like. The required dosage will vary with the particular condition being treated, with the severity of the condition and with the duration of desired treatment, and multiple dosages may be used for a single day. In order to block the stress-related effects of endogenous CRF within the central nervous system, it may be necessary to deliver the CRF antagonists into the cerebral ventricle or spinal fluid. Alternatively, a means of modifying the antagonists so that they could penetrate the blood-brain barrier should be found. For parenteral administration, solutions in peanut oil, in aqueous propylene glycol, or in sterile aqueous solution may be employed; sterile aqueous media are readily available. Such aqueous solutions, which are suitably buffered, are especially suitable for intravenous (iv), intramuscular, subcutaneous (s.c.) and intraperitoneal administration. For s.c. administration, corn oil or a 3–6% mannitol solution may be preferred.

Such peptides are often administered in the form of pharmaceutically acceptable nontoxic salts, such as acid addition salts or metal complexes. The salts of trifluoroacetic acid and pamoic acid may be preferred. It may also be desirable to deliver the CRF antagonist peptide over prolonged periods of time, for example, for periods of one week or considerably longer, from a single administration, and slow release, depot or implant dosage forms may be utilized.

The peptides should be administered under the guidance of a physician in single or multiple doses, and pharmaceutical compositions will usually contain the peptide in conjunction with a known, pharmaceutically-acceptable carrier that may extend its duration of action. The effective dosage generally depends on the intended route of administration and other factors such as age and weight of the patient, as generally known to a physician, and also upon the illness being treated. Usually, the dosage will be from about 0.01 to about 10 milligrams of the peptide per kilogram of the body weight of the host animal. For the treatment of inflammatory diseases about 0.1 to about 100 mg/kg is generally employed; for gastrointestinal diseases about 0.1 to about 50 mg/kg, as well as for anorexia nervosa, hemorrhagic stress, treatment of drug and alcohol withdrawal symptoms and treatment of fertility problems. The daily dosage may be given in a single dose or up to three divided doses.

As used herein all temperatures are ° C. and all ratios are by volume. Percentages of liquid materials are also by volume. By lower alkyl is meant $C_1$ to $C_6$.

Although the invention has been described with regard to its preferred embodiments, it should be understood that various changes and modifications as would be obvious to one having the ordinary skill in this art may be made without departing from the scope of the invention which is set forth in the claims appended hereto. For example, pharmaceutically acceptable salts, although not specifically recited, are clearly known equivalents of the claimed subject matter. Instead of D-Phe at the 12-position, L-Phe or Tyr or another appropriate D-isomer generally similar to those hereinbefore mentioned, e.g., D-Cpa, may be present and is considered to be equivalent, although a D-isomer is preferred. D-Ala$^{31}$ can be substituted for Ala$^{31}$ with retention of biopotency well above that of the native sequence, thus, it is considered an equivalent at the 31-position. Instead of the simple amide at the C-terminus, a lower alkyl-substituted amide, i.e., 1–4 carbon atoms, e.g., methylamide or ethylamide, may be incorporated. An equivalent lactam bond can also be created by linking the side chains of Lys$^{30}$ and Glu$^{33}$; however, the bonds illustrated hereinbefore are preferred. The amino group which is reacted to form the 30–33 lactam cyclizing bond or the α-amino group of one of the residues in positions 30 through 33 may be alkylated, as by adding a methyl group, such changes are considered to create equivalent cyclic peptides. Likewise when a D- or L-isomer of Aph, Lys, Orn, Dbu, Dpr, Arg, or Agl is present in the 32-position, its side chain may also be optionally alkylated by a lower alkyl group, e.g., methyl or ethyl. Such aforementioned peptides are considered as being within the scope of the invention.

SEQUENCE LISTING SUMMARY

SEQ ID NO:1, when the C-terminus is amidated, is the amino acid sequence of ovine CRF.

SEQ ID NO:2, when the C-terminus is amidated, is the amino acid sequence of rat/human CRF.

SEQ ID NO:3, when pGlu is at the N-terminus and the C-terminus is amidated, is the amino acid sequence of frog sauvagine.

SEQ ID NO:4, when the C-terminus is amidated, is the amino acid sequence of α-helical CRF, referred to as "AHC".

SEQ ID NO:5, when the C-terminus is amidated, is the amino acid sequence of porcine CRF.

SEQ ID NO:6, when the C-terminus is amidated, is the amino acid sequence of bovine CRF.

SEQ ID NO:7, when the C-terminus is amidated, is the amino acid sequence of fish CRF.

SEQ ID NO:8, when the C-terminus is amidated, is the amino acid sequence of carp urotensin.

SEQ ID NO:9, when the C-terminus is amidated, is the amino acid sequence of suckerfish urotensin.

SEQ ID No:10, when the C-terminus is amidated, is the amino acid sequence of flathead (Maggy) sole urotensin.

SEQ ID NO:11, when the C-terminus is amidated, is the amino acid sequence of flounder urotensin.

What is claimed is:

1. A cyclic peptide which is an antagonist of CRF, said peptide having the formula:

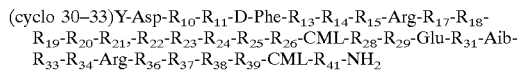

wherein Y is an acyl group having up to 15 carbon atoms; $R_{10}$ is Leu or CML; $R_{11}$ is Thr or Ser; $R_{13}$ is His, Tyr or Glu; $R_{14}$ is CML or Leu; $R_{15}$ is Leu or CML; $R_{17}$ is Glu, CML, Asn or Lys; $R_{18}$ is Val, Nle, CML or Met; $R_{19}$ is Leu or Ile; $R_{20}$ is Glu, D-Glu, or His; $R_{21}$ is Nle or Met; $R_{22}$ is Ala, D-Ala, Aib, Asp, Thr, D-Thr, Glu or D-Glu; $R_{23}$ is Arg or Lys; $R_{24}$ is Ala, Aib or CML; $R_{25}$ is Glu or Asp; $R_{26}$ is Gln, Asn or Lys; $R_{28}$ is Ala, Lys, Aib or Arg; $R_{29}$ is Gln, Aib or Glu; $R_{31}$ is Aib or an L-isomer of an α-amino acid other than Cys; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{38}$ is Nle, Met or CML; $R_{39}$ is Glu, Aib or Asp; and $R_{41}$ is Ala, Aib, Ile, Gly, Val, Leu, CML, Nle, Phe, Nva or Gln; wherein D-Phe$^{12}$ may be substituted by another D-amino acid, such as D-Leu, D-Tyr, D-Trp, D-Cpa, D-Trp, D-Nal or D-Pal, or by Phe or Tyr.

2. A cyclic CRF antagonist peptide according to claim 1 having the formula:

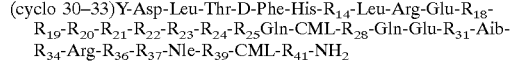

wherein Y is an acyl group having not more than 7 carbon atoms; $R_{14}$ is Leu or CML; $R_{18}$ is Val, CML or Nle; $R_{19}$ is Leu or Ile; $R_{20}$ is Glu or D-Glu; $R_{21}$ is Nle or Met; $R_{22}$ is Ala, D-Ala, Aib or Thr; $R_{23}$ is Arg or Lys; $R_{24}$ is Ala or Aib; $R_{25}$ is Asp or Glu; $R_{28}$ is Ala or Aib; $R_{31}$ is Ala or Aib; $R_{33}$ is Lys or Orn; $R_{34}$ is Aib or Asn; $R_{36}$ is Lys or CML; $R_{37}$ is Leu or CML; $R_{39}$ is Glu or Asp; and $R_{41}$ is Ala, Aib, CML or Ile.

3. A cyclic CRF antagonist peptide according to claim 1 having the formula:

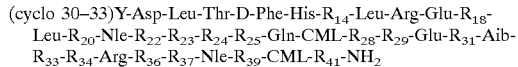

wherein Y is Ac, Acr or For; $R_{14}$ is Leu or CML; $R_{18}$ is Val, CML or Nle; $R_{20}$ is Glu or D-Glu; $R_{22}$ is Ala, Aib, D-Ala or Thr; $R_{23}$ is Arg or Lys; $R_{24}$ is Ala or Aib; $R_{25}$ is Asp or Glu; $R_{28}$ is Ala or Aib; $R_{29}$ is Gln or Glu; $R_{31}$ is Ala or Aib; $R_{33}$ is Lys or Orn; $R_{34}$ is Asn or Aib; $R_{36}$ is Lys, CML or Leu; $R_{37}$ is Leu or CML; $R_{39}$ is Glu or Asp; and $R_{41}$ is Ile, Aib, CML or Ala; provided that D-2Nal or D-Leu or Phe may be substituted for D-Phe.

4. A cyclic CRF antagonist peptide according to claim 1 having the formula:

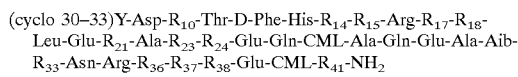

wherein Y is Ac, For or Acr; $R_{10}$ is Leu or CML; $R_{14}$, $R_{15}$, and $R_{37}$ are independently Leu or CML; $R_{17}$ is Glu or CML; $R_{18}$ is Val or CML; $R_{21}$ is Met or Nle; $R_{23}$ is Arg or Lys; $R_{24}$ is Ala or CML; $R_{33}$ is Lys or Orn; $R_{36}$ is Lys or CML; $R_{38}$ is Met, Nle or CML; and $R_{41}$ is Ile or CML; and wherein at least one of $R_{14}$, $R_{18}$, $R_{36}$, $R_{37}$, and $R_{41}$ is CML.

5. A cyclic CRF antagonist peptide according to claim 1 having the formula:

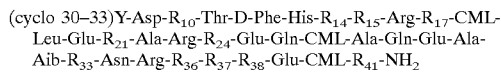

wherein Y is Ac, For or Acr; $R_{10}$ is Leu or CML; $R_{14}$, $R_{15}$, and $R_{37}$ are independently Leu or CML; $R_{17}$ is Glu or CML; $R_{21}$ is Met or Nle; $R_{24}$ is Ala or CML; $R_{33}$ is Lys or Orn; $R_{36}$ is Lys or CML; $R_{38}$ is Met, Nle or CML; and $R_{41}$ is Ile or CML.

6. A cyclic peptide according to claim 1 having the formula:

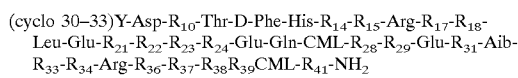

wherein Y is an acyl group having up to 15 carbon atoms; $R_{10}$, R14, $R_{15}$, and $R_{37}$ are independently Leu or CML; $R_{17}$ is Glu or CML; $R_{18}$ is Val or CML; $R_{21}$ is Met or Nle; $R_{22}$, $R_{28}$ and $R_{31}$ are independently either Ala or Aib; $R_{23}$ is Arg or Lys; $R_{24}$ is Ala, Aib or CML; $R_{29}$ is Gln or Aib; $R_{33}$ is Lys or Orn; $R_{34}$ is Asn or Aib; $R_{36}$ is Lys or CML; $R_{38}$ is Met, Nle or CML; $R_{39}$ is Glu or Aib; and $R_{41}$ is Leu, CML or Aib; and wherein at least one of $R_{22}$, $R_{24}$, $R_{28}$, and $R_{31}$ is Aib.

7. A cyclic peptide according to claim 6 wherein at least one of $R_{14}$, $R_{18}$, and $R_{37}$ is CML.

8. A cyclic CRF antagonist peptide according to claim 1 wherein $R_{18}$ is Val, $R_{22}$ is Ala, $R_{23}$ is Arg, $R_{24}$ is Ala, $R_{25}$ is Glu, $R_{28}$ is Ala, $R_{39}$ is Glu, and $R_{41}$ is Ile.

9. A cyclic CRF antagonist peptide according to claim 1 having the formula:

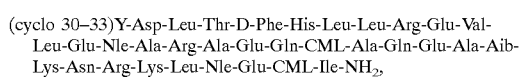

wherein Y is an acyl group having not more than 12 carbon atoms.

10. A cyclic CRF antagonist peptide according to claim 1 having the formula:

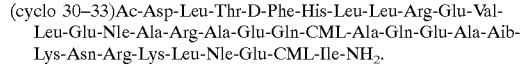

11. A method of treating stress-induced depression or anxiety, which method comprises administering an effective amount of a cyclic CRF antagonist peptide according to claim 1.

12. A cyclic peptide which is an antagonist of CRF, said peptide having the formula:

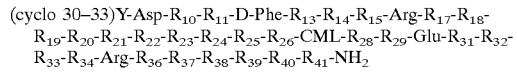

wherein Y is an acyl group having up to 15 carbon atoms; $R_{10}$ is Leu or CML; $R_{11}$ is Thr or Ser; $R_{13}$ is His, Tyr or Glu; $R_{14}$ is CML or Leu; $R_{15}$ is Leu or CML; $R_{17}$ is Glu, CML, Asn or Lys; Rls is Val, Nle, CML or Met; $R_{19}$ is Leu or Ile; $R_{20}$ is Glu, D-Glu, or His; $R_{21}$ is Nle or Met; $R_{22}$ is Ala, D-Ala, Aib, Asp, Thr, D-Thr, Glu or D-Glu; $R_{23}$ is Arg or Lys; $R_{24}$ is Ala, Aib or CML; $R_{25}$ is Glu or Asp; $R_{26}$ is Gln, Asn or Lys; $R_{28}$ is Ala, Lys, Aib or Arg; $R_{29}$ is Gln, Aib or Glu; $R_{31}$ is Aib or an L-isomer of an α-amino acid other than Cys; $R_{32}$ is Aib or a D- or L-isomer of an α-amino acid other than Cys; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{38}$ is Nle, Met or CML; $R_{39}$ is Glu, Aib or Asp; $R_{40}$ is CML, Ile, Aib, Thr, Asn, Glu, Ala, Val, Leu, Nle, Phe, Nva, Gly or Gln; and $R_{41}$ is Ala, Aib, Ile, Gly, Val, Leu, CML, Nle, Phe, Nva or Gln; wherein D-Phe[12] may be substituted by another D-amino acid, such as D-Leu, D-Tyr, D-Trp, D-Cpa, D-Trp, D-Nal or D-Pal, or by Phe or Tyr; provided, however, that either $R_{18}$ or $R_{40}$ is CML and that at least one of $R_{22}$, $R_{24}$, $R_{28}$, $R_{31}$ and $R_{32}$ is Aib.

13. A cyclic CRF antagonist peptide according to claim 12 wherein $R_{32}$ and $R_{41}$ are Aib.

14. A cyclic peptide which is an antagonist of CRF, said peptide having the formula:

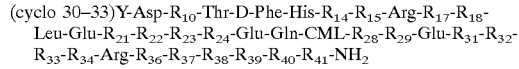

wherein Y is an acyl group having up to 15 carbon atoms; $R_{10}$, $R_{14}$, $R_{15}$, and $R_{37}$ are independently Leu or CML; $R_{17}$ is Glu or CML; $R_{18}$ is Val or CML; $R_{21}$ is Met or Nle; $R_{22}$, $R_{28}$ and $R_{31}$ are independently either Ala or Aib; $R_{23}$ is Arg or Lys; $R_{24}$ is Ala, Aib or CML; $R_{29}$ is Gln or Aib; $R_{32}$ is His, Aib, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{34}$ is Asn or Aib; $R_{36}$ is Lys or CML; $R_{38}$ is Met, Nle or CML; $R_{39}$ is Glu or Aib; $R_{40}$ is CML, Ile or Aib; and $R_{41}$ is Leu, CML or Aib; provided that either $R_{18}$ or $R_{40}$ is CML and that at least one of $R_{22}$, $R_{24}$, $R_{28}$, and $R_{31}$ is Aib.

15. A method of treating stress-induced depression or anxiety, which method comprises administering an effective amount of a cyclic CRF antagonist peptide according to claim 14.

16. A cyclic peptide according to claim 14 wherein $R_{29}$ is Aib.

17. A cyclic peptide according to claim 14 having one of the following formulas:

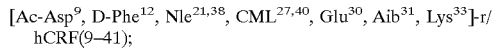

[Ac-Asp$^9$, D-Phe$^{12}$, Nle$^{21,38}$, Aib$^{22}$, CML$^{27,40}$, Glu$^{30}$, Lys$^{33}$]-r/hCRF(9–41);

[Ac-Asp$^9$, D-Phe$^{12}$, Nle$^{21,38}$, Aib$^{24}$, CML$^{27,40}$, Glu$^{30}$, Lys$^{33}$]-r/hCRF(9–41);

and

[Ac-Asp$^9$, D-Phe$^{12}$, Nle$^{21,38}$, CML$^{27,40}$, Aib$^{28}$, Glu$^{30}$, Lys$^{33}$]-r/hCRF(9–41).

18. A method of treating stress-induced depression or anxiety, which method comprises administering an effective amount of a cyclic CRF antagonist peptide according to claim 17.

* * * * *

UNITED STATES PATENT AND TRADEMARK OFFICE
CERTIFICATE OF CORRECTION

PATENT NO. : 6,323,312 B1
DATED : November 27, 2001
INVENTOR(S) : Rivier

It is certified that error appears in the above-identified patent and that said Letters Patent is hereby corrected as shown below:

Column 1,
After line 8, insert, as an initial paragraph:
  -- This invention was made with Government support under Grant No. DK-26741 awarded by the National Institutes of Health. The Government has certain rights in this invention. --

Column 32,
Line 21, "R1s" should be -- $R_{18}$ --.

Signed and Sealed this

Thirtieth Day of July, 2002

Attest:

JAMES E. ROGAN
Attesting Officer          Director of the United States Patent and Trademark Office

SEQUENCE LISTING

```
(1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 1:

Ser Gln Glu Pro Pro Ile Ser Leu Asp Leu Thr Phe His Leu Leu Arg
  1               5                  10                  15

Glu Val Leu Glu Met Thr Lys Ala Asp Gln Leu Ala Gln Gln Ala His
             20                  25                  30
```

```
Ser Asn Arg Lys Leu Leu Asp Ile Ala
        35                  40
```

(2) INFORMATION FOR SEQ ID NO: 2:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 2:

```
Ser Glu Glu Pro Pro Ile Ser Leu Asp Leu Thr Phe His Leu Leu Arg
 1               5                  10                  15
Glu Val Leu Glu Met Ala Arg Ala Glu Gln Leu Ala Gln Gln Ala His
                20                  25                  30
Ser Asn Arg Lys Leu Met Glu Ile Ile
        35                  40
```

(2) INFORMATION FOR SEQ ID NO: 3:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO: 3:

```
Glu Gly Pro Pro Ile Ser Ile Asp Leu Ser Leu Glu Leu Leu Arg Lys
 1               5                  10                  15
Met Ile Glu Ile Glu Lys Gln Glu Lys Glu Lys Gln Gln Ala Ala Asn
                20                  25                  30
Asn Arg Leu Leu Leu Asp Thr Ile
        35                  40
```

(2) INFORMATION FOR SEQ ID NO: 4:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO: 4:

```
Ser Gln Glu Pro Pro Ile Ser Leu Asp Leu Thr Phe His Leu Leu Arg
 1               5                  10                  15
Glu Met Leu Glu Met Ala Lys Ala Glu Gln Glu Ala Glu Gln Ala Ala
                20                  25                  30
Leu Asn Arg Leu Leu Leu Glu Glu Ala
        35                  40
```

(2) INFORMATION FOR SEQ ID NO: 5:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO: 5:

```
Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
             20                  25                  30

Ser Asn Arg Lys Leu Met Glu Asn Phe
         35                  40
```

(2) INFORMATION FOR SEQ ID NO: 6:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO: 6:

```
Ser Gln Glu Pro Pro Ile Ser Leu Asp Leu Thr Phe His Leu Leu Arg
 1               5                  10                  15

Glu Val Leu Glu Met Thr Lys Ala Asp Gln Leu Ala Gln Gln Ala His
             20                  25                  30

Asn Asn Arg Lys Leu Leu Asp Ile Ala
         35                  40
```

(2) INFORMATION FOR SEQ ID NO: 7:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 7:

```
Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
             20                  25                  30

Ser Asn Arg Lys Met Met Glu Ile Phe
         35                  40
```

(2) INFORMATION FOR SEQ ID NO: 8:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 8:

```
Asn Asp Asp Pro Pro Ile Ser Ile Asp Leu Thr Phe His Leu Leu Arg
 1               5                  10                  15

Asn Met Ile Glu Met Ala Arg Asn Glu Asn Gln Arg Glu Gln Ala Gly
             20                  25                  30

Leu Asn Arg Lys Tyr Leu Asp Glu Val
         35                  40
```

(2) INFORMATION FOR SEQ ID NO: 9:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 9:

```
Asn Asp Asp Pro Pro Ile Ser Ile Asp Leu Thr Phe His Leu Leu Arg
 1               5                  10                      15

Asn Met Ile Glu Met Ala Arg Ile Glu Asn Glu Arg Glu Gln Ala Gly
                20                  25                  30

Leu Asn Arg Lys Tyr Leu Asp Glu Val
                35              40
```

(2) INFORMATION FOR SEQ ID NO: 10:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 10:

```
Ser Glu Glu Pro Pro Met Ser Ile Asp Leu Thr Phe His Met Leu Arg
 1               5                  10                      15

Asn Met Ile His Arg Ala Lys Met Glu Gly Glu Arg Glu Gln Ala Leu
                20                  25                  30

Ile Asn Arg Asn Leu Leu Asp Glu Val
                35              40
```

(2) INFORMATION FOR SEQ ID NO: 11:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO: 11:

```
Ser Glu Asp Pro Pro Met Ser Ile Asp Leu Thr Phe His Met Leu Arg
 1               5                  10                      15

Asn Met Ile His Met Ala Lys Met Glu Gly Glu Arg Glu Gln Ala Gln
                20                  25                  30

Ile Asn Arg Asn Leu Leu Asp Glu Val
                35              40
```